(12) United States Patent
Forsell

(10) Patent No.: US 11,065,041 B2
(45) Date of Patent: **\*Jul. 20, 2021**

(54) DEVICE AND METHOD FOR BONE ADJUSTMENT WITH ANCHORING FUNCTION

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 7 days.

This patent is subject to a terminal disclaimer.

(21) Appl. No.: 15/973,551

(22) Filed: May 8, 2018

(65) Prior Publication Data

US 2018/0317980 A1 Nov. 8, 2018

Related U.S. Application Data

(63) Continuation of application No. 13/123,536, filed as application No. PCT/SE2009/051232 on Oct. 29, 2009, now Pat. No. 9,962,199.

(Continued)

(30) Foreign Application Priority Data

Oct. 31, 2008 (SE) .................................. 0802153-7

(51) Int. Cl.
*A61B 17/72* (2006.01)
*A61B 17/68* (2006.01)
(Continued)

(52) U.S. Cl.
CPC .......... *A61B 17/7216* (2013.01); *A61B 17/68* (2013.01); *A61B 17/7016* (2013.01);
(Continued)

(58) Field of Classification Search
CPC ........................................... A61B 17/72–7275
See application file for complete search history.

(56) References Cited

U.S. PATENT DOCUMENTS 5,263,955 A * 11/1993 Baumgart .......... A61B 17/7216
606/62
5,314,426 A * 5/1994 Pohl ........................ A61B 17/66
606/58

(Continued)

*Primary Examiner* — Eduardo C Robert
*Assistant Examiner* — Michelle C Eckman

(57) ABSTRACT

A device for bone adjustment in a mammal. The device comprising two or more anchoring devices adapted to implanted intramedullary and attached to a bone in said mammal and an adjustment device for exerting force on said anchoring devices, said adjustment device being adapted to postoperatively adjust at least one of the distance between or orientation of, at least two of said anchoring devices. The operation device further comprises a motor and said operation device is adapted to operate said adjustment device. The operation device further comprises a gearbox connected to the motor, wherein an outgoing speed from the gear box is lower than the speed by the motor alone, accomplished by the gearbox, and wherein the outgoing speed of the gearbox is less than 10 turn per second during normal operation. The device also comprises a control device adapted to control the operation device, wherein the control device is: programmed to control the device according to a pre-programmed time-schedule, and programmed to control the device based on input from a sensor or measuring device sensing any possible physical parameter of the patient or any functional parameter of the system.

36 Claims, 25 Drawing Sheets

Related U.S. Application Data

(60) Provisional application No. 61/227,808, filed on Jul. 23, 2009.

(51) Int. Cl.

| | | |
|---|---|---|
| *A61B 17/70* | (2006.01) | |
| *A61B 17/66* | (2006.01) | |
| *A61B 17/00* | (2006.01) | |
| *A61B 90/00* | (2016.01) | |

(52) U.S. Cl.
CPC ...... *A61B 17/7017* (2013.01); *A61B 17/7062* (2013.01); *A61B 17/7258* (2013.01); *A61B 17/66* (2013.01); *A61B 17/7233* (2013.01); *A61B 17/7291* (2013.01); *A61B 2017/00212* (2013.01); *A61B 2017/00398* (2013.01); *A61B 2017/00411* (2013.01); *A61B 2017/00539* (2013.01); *A61B 2090/061* (2016.02)

(56) References Cited

U.S. PATENT DOCUMENTS

| | | | | |
|---|---|---|---|---|
| 5,350,379 A * | 9/1994 | Spievack | A61B 17/7216 | 606/63 |
| 5,356,411 A * | 10/1994 | Spievack | A61B 17/7275 | 606/63 |
| 5,415,660 A * | 5/1995 | Campbell | A61B 17/7216 | 606/62 |
| 5,466,261 A * | 11/1995 | Richelsoph | A61F 2/36 | 606/60 |
| 5,505,733 A * | 4/1996 | Justin | A61B 17/7216 | 606/63 |
| 5,536,269 A * | 7/1996 | Spievack | A61B 17/7216 | 606/63 |
| 5,626,579 A * | 5/1997 | Muschler | A61B 17/7216 | 606/60 |
| 5,626,581 A * | 5/1997 | Staehlin | A61B 17/7216 | 606/53 |
| 5,704,938 A * | 1/1998 | Staehlin | A61B 17/7216 | 606/105 |
| 5,961,553 A * | 10/1999 | Coty | A61B 17/7216 | 606/62 |
| 6,033,412 A * | 3/2000 | Losken | A61B 17/663 | 606/105 |
| 6,416,516 B1 * | 7/2002 | Stauch | A61B 17/7216 | 606/62 |
| 6,673,079 B1 * | 1/2004 | Kane | A61B 17/663 | 606/105 |
| 6,918,910 B2 * | 7/2005 | Smith | A61B 17/8076 | 606/57 |
| 7,060,075 B2 * | 6/2006 | Govari | A61B 17/1707 | 606/98 |
| 7,135,022 B2 * | 11/2006 | Kosashvili | A61B 17/7216 | 606/63 |
| 7,955,357 B2 * | 6/2011 | Kiester | A61B 17/7004 | 606/258 |
| 8,623,092 B2 * | 1/2014 | Bickley | A61F 2/40 | 623/18.11 |
| 9,078,711 B2 * | 7/2015 | Quick | A61B 17/7016 | |
| 9,179,938 B2 * | 11/2015 | Pool | A61B 17/7016 | |
| 9,579,203 B2 * | 2/2017 | Soubeiran | A61B 17/7216 | |
| 9,636,153 B2 * | 5/2017 | Stauch | A61B 17/7216 | |
| 9,962,199 B2 * | 5/2018 | Forsell | A61B 17/68 | |
| 10,092,328 B2 * | 10/2018 | Sharifi-Mehr | A61B 17/7011 | |
| 10,405,891 B2 * | 9/2019 | Pool | A61B 17/7016 | |
| 10,420,666 B2 * | 9/2019 | Baym | A61F 5/0102 | |
| 2005/0055025 A1 * | 3/2005 | Zacouto | A61B 17/6491 | 623/17.12 |
| 2005/0234448 A1 * | 10/2005 | McCarthy | A61B 17/8004 | 606/57 |
| 2006/0069447 A1 * | 3/2006 | DiSilvestro | A61F 2/389 | 623/23.16 |
| 2007/0055219 A1 * | 3/2007 | Whitman | A61B 17/00234 | 606/1 |
| 2007/0267281 A1 * | 11/2007 | Smith | A61B 17/00 | 200/61.53 |
| 2008/0108995 A1 * | 5/2008 | Conway | A61B 17/7216 | 606/63 |
| 2009/0036892 A1 * | 2/2009 | Karidis | A61B 17/62 | 606/60 |
| 2009/0062798 A1 * | 3/2009 | Conway | A61B 17/7216 | 606/63 |
| 2009/0062886 A1 * | 3/2009 | O'Handley | A61N 1/3787 | 607/51 |
| 2009/0112207 A1 * | 4/2009 | Walker | A61B 17/7016 | 606/57 |
| 2009/0254088 A1 * | 10/2009 | Soubeiran | A61B 17/7216 | 606/63 |
| 2010/0049204 A1 * | 2/2010 | Soubeiran | A61B 17/025 | 606/90 |
| 2010/0094302 A1 * | 4/2010 | Pool | A61B 17/7004 | 606/90 |
| 2010/0121323 A1 * | 5/2010 | Pool | A61B 17/7004 | 606/54 |
| 2010/0318085 A1 * | 12/2010 | Austin | A61B 17/0642 | 606/62 |
| 2011/0060336 A1 * | 3/2011 | Pool | A61B 17/1725 | 606/57 |
| 2011/0196371 A1 * | 8/2011 | Forsell | A61B 17/68 | 606/62 |
| 2011/0230883 A1 * | 9/2011 | Zahrly | A61B 17/7216 | 606/63 |
| 2012/0209269 A1 * | 8/2012 | Pool | A61B 17/1725 | 606/63 |
| 2012/0296234 A1 * | 11/2012 | Wilhelm | A61B 17/66 | 600/587 |
| 2013/0023876 A1 * | 1/2013 | Rabiner | A61B 17/7097 | 606/63 |
| 2014/0114311 A1 * | 4/2014 | Pool | A61B 17/84 | 606/62 |
| 2014/0155946 A1 * | 6/2014 | Skinlo | A61B 17/8852 | 606/86 R |
| 2014/0236311 A1 * | 8/2014 | Vicatos | A61B 17/7216 | 623/23.47 |
| 2015/0105834 A1 * | 4/2015 | Bilger | A61B 17/7001 | 606/86 R |
| 2016/0183994 A1 * | 6/2016 | Quach | A61B 17/8866 | 606/90 |
| 2016/0367297 A1 * | 12/2016 | Nill | A61B 17/7016 | |
| 2017/0172624 A1 * | 6/2017 | Brunner | A61B 17/7016 | |
| 2018/0296256 A1 * | 10/2018 | Beckett | A61B 17/8605 | |
| 2019/0015138 A1 * | 1/2019 | Schwardt | A61B 17/7216 | |
| 2019/0105086 A1 * | 4/2019 | Janda | A61B 17/7216 | |
| 2019/0133650 A1 * | 5/2019 | Haaja | A61B 17/66 | |
| 2019/0254712 A1 * | 8/2019 | Roschak | A61B 17/68 | |
| 2019/0274742 A1 * | 9/2019 | Garlock | A61B 17/7291 | |

\* cited by examiner

"Prior art"

Fig.4
Fig.5
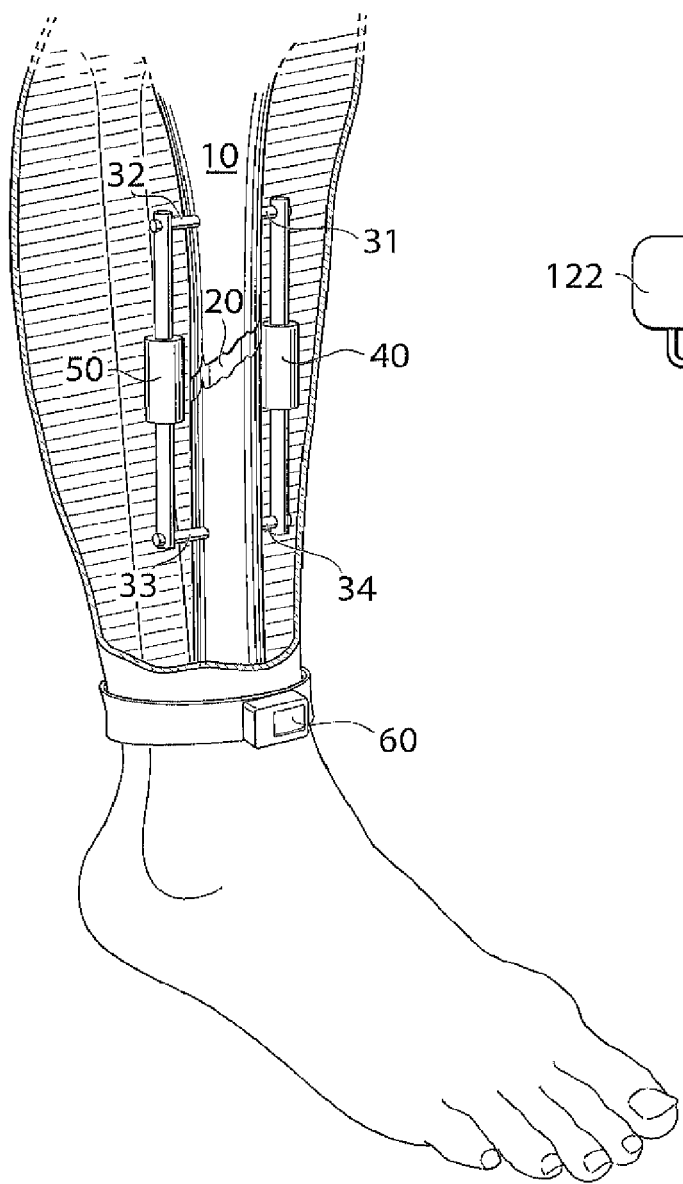
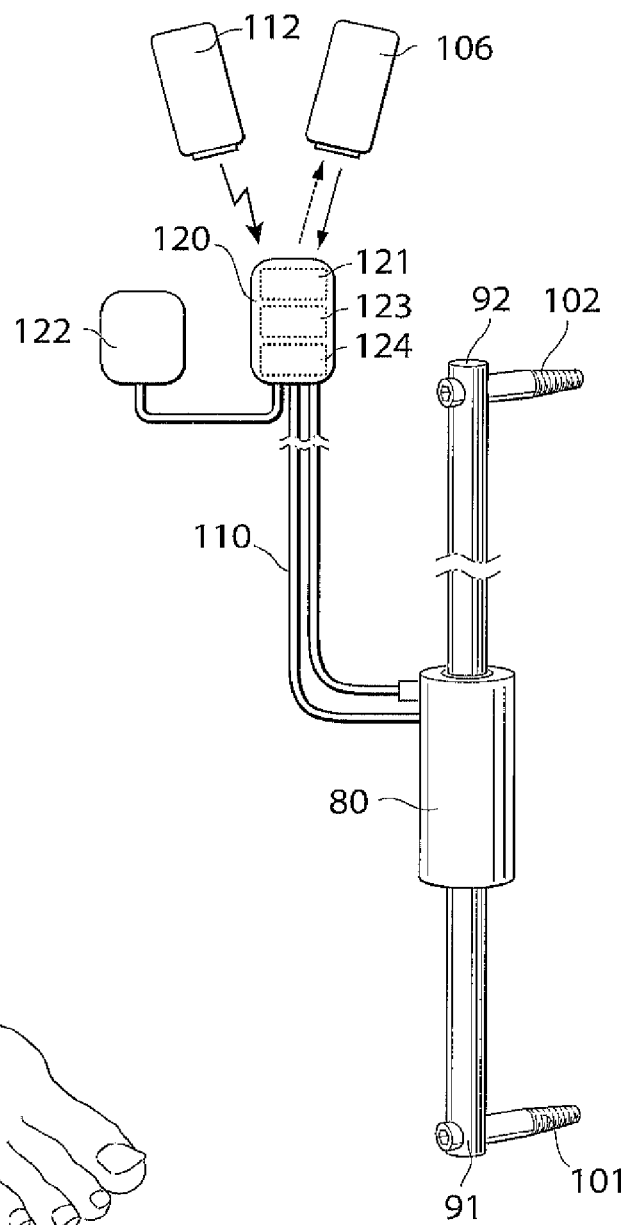

Fig. 8 a
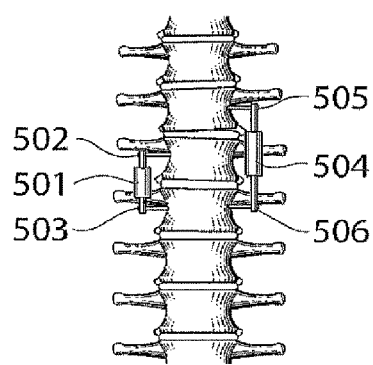
Fig. 8 b
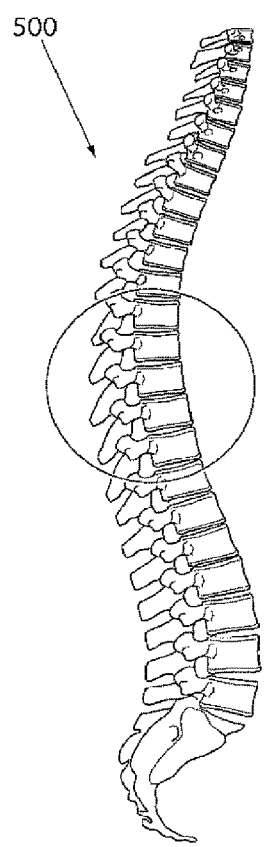
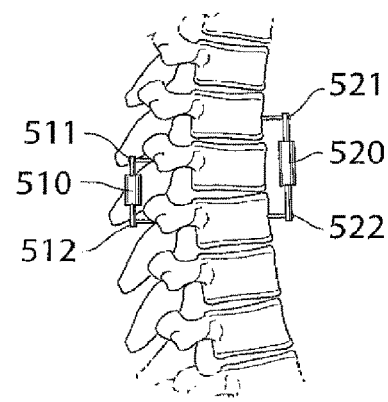
Fig. 8 c

Fig. 9 e
Fig. 9 f
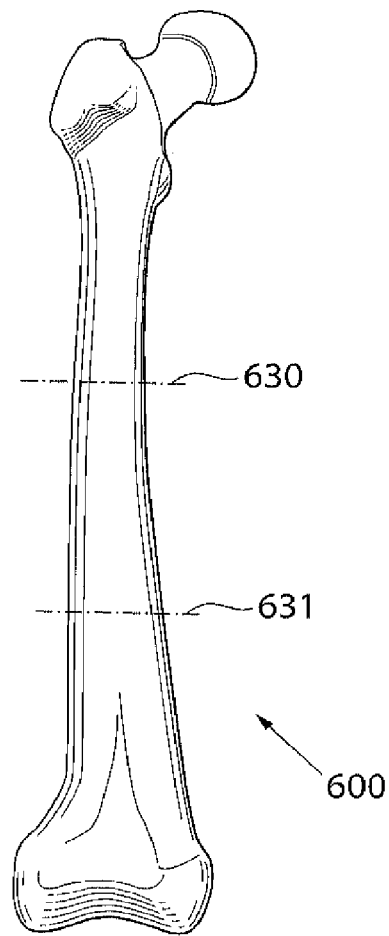
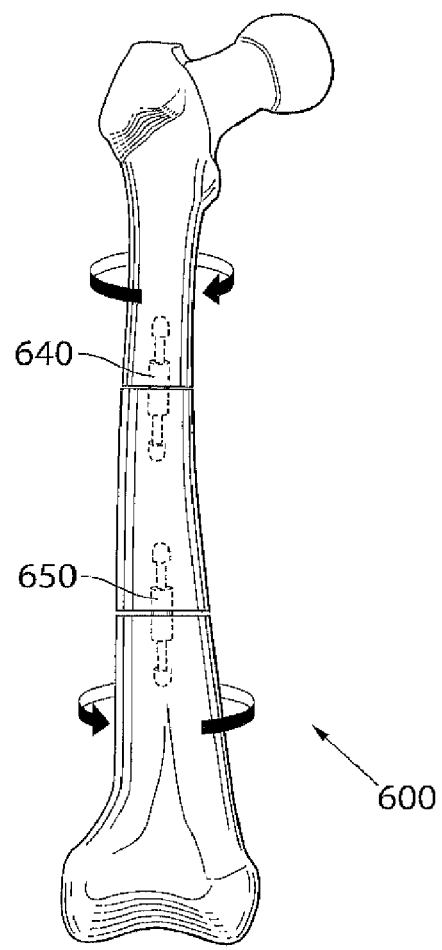

Fig. 12a
Fig. 12b
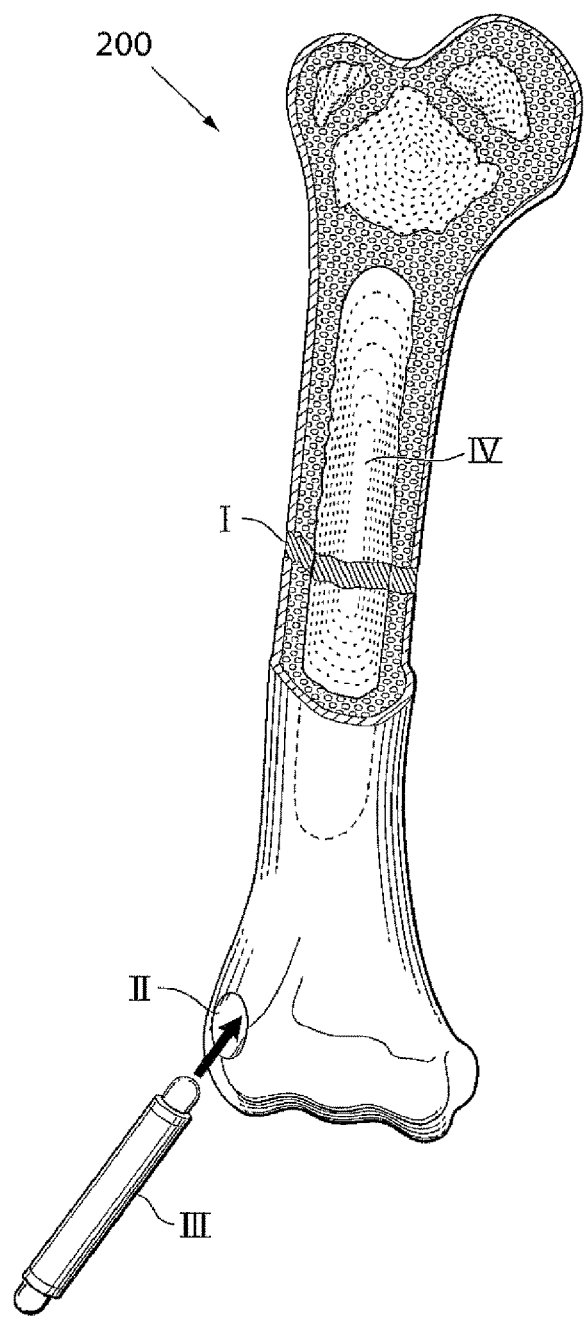
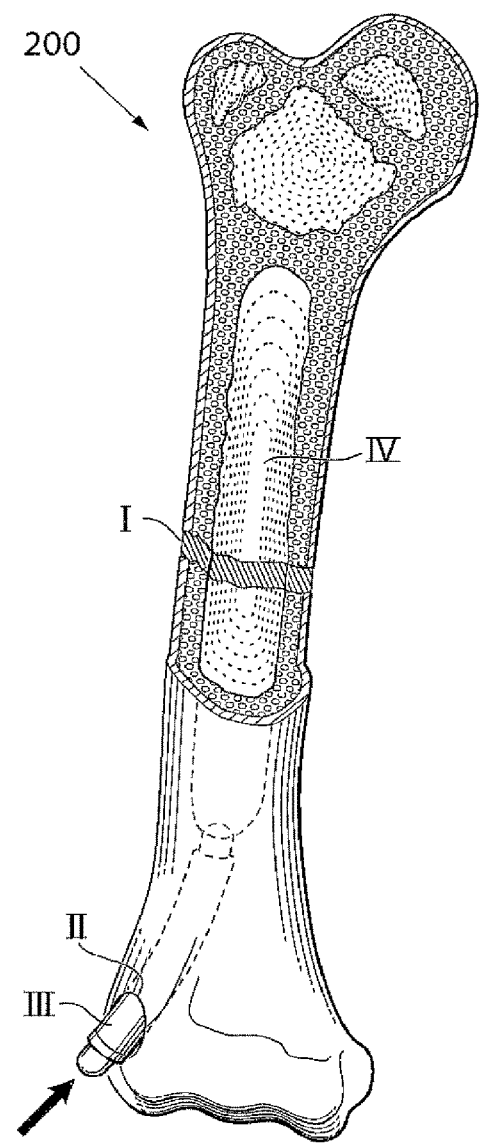

Fig. 12c
Fig. 12d
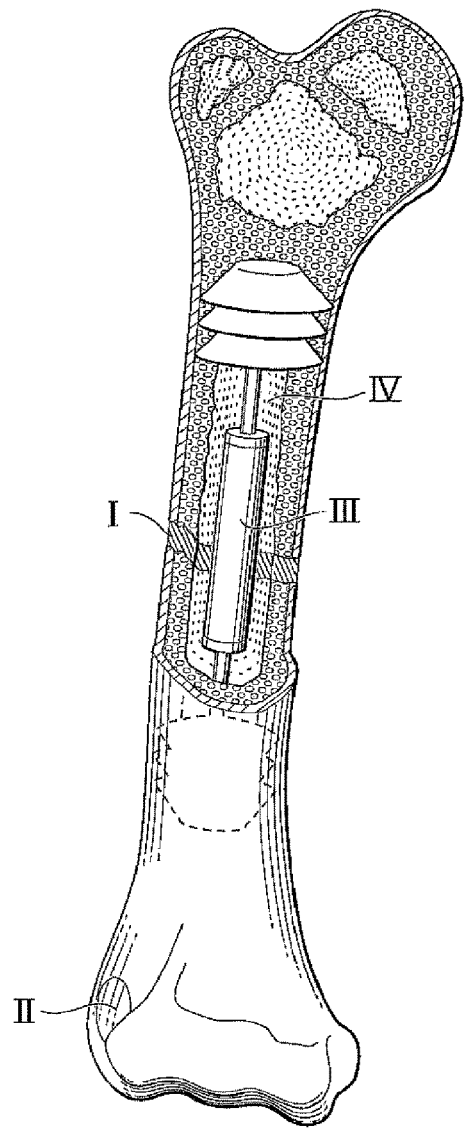
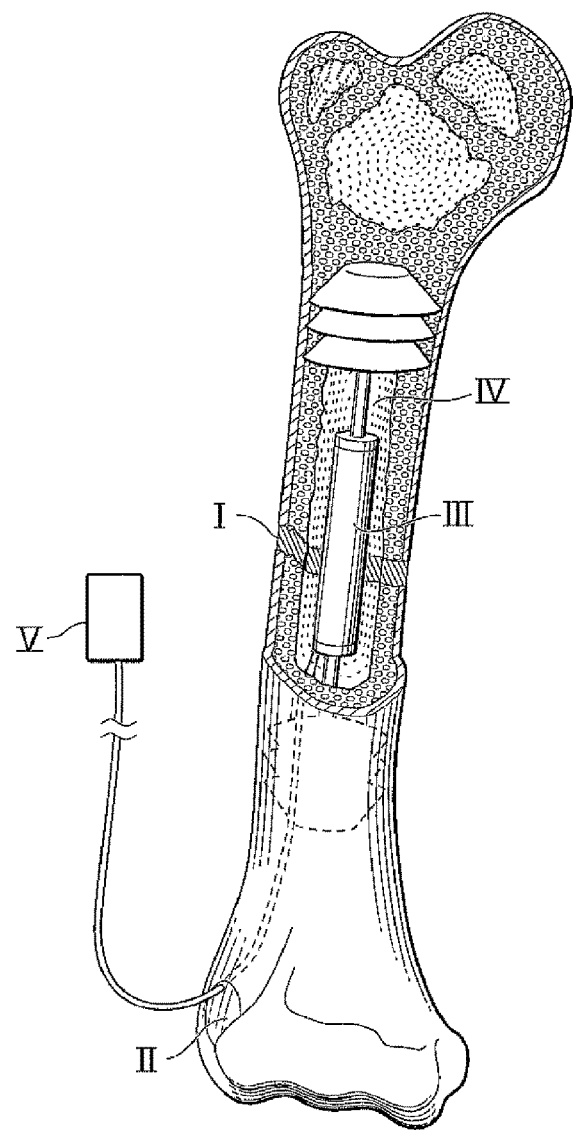

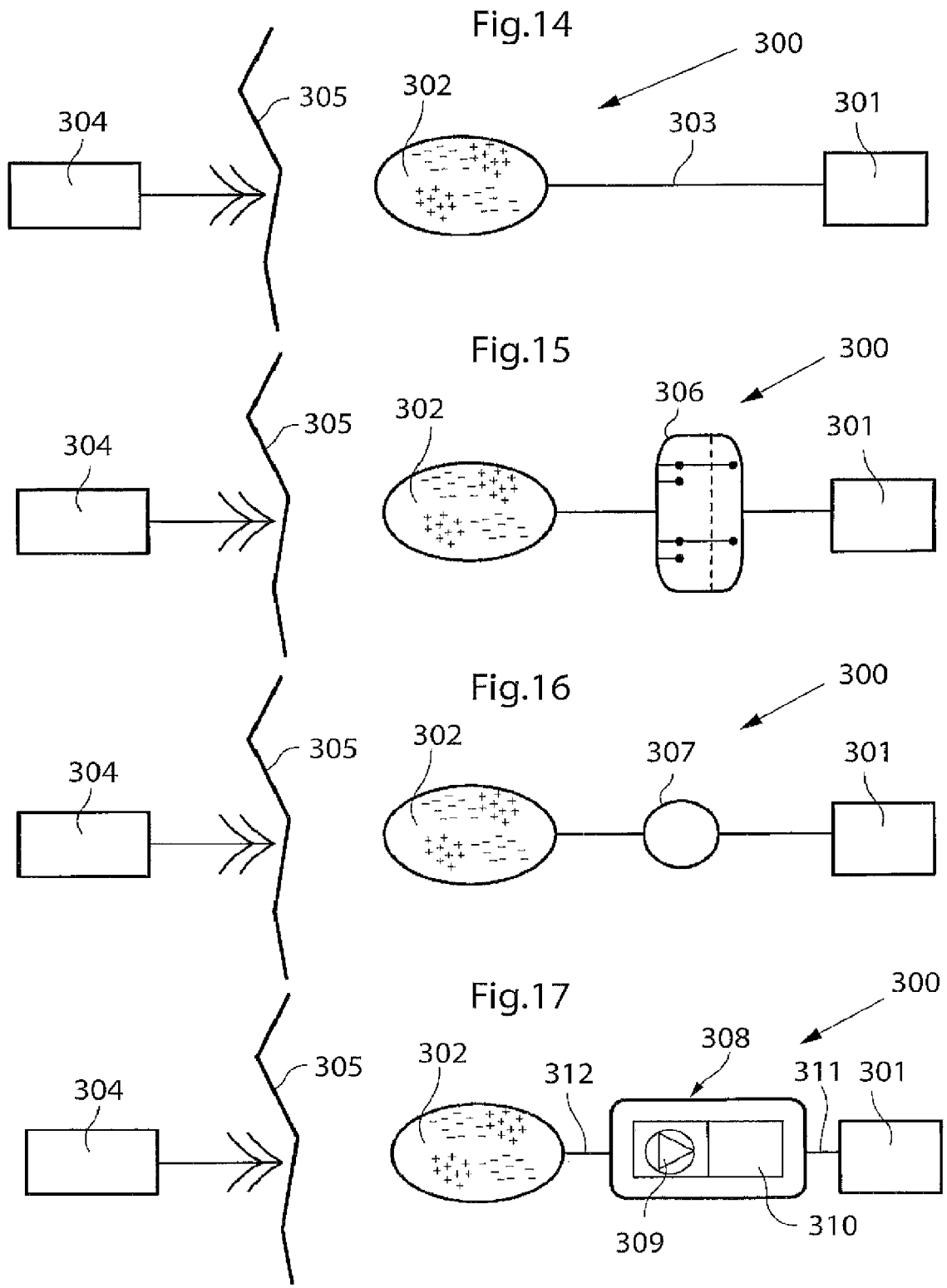

DEVICE AND METHOD FOR BONE ADJUSTMENT WITH ANCHORING FUNCTION

This application is a continuation of U.S. application Ser. No. 13/123,538 filed on Apr. 11, 2011, which is the U.S. national phase of International Application No. PCT/SE2009/051232, filed Oct. 29, 2009, which designated the U.S. and claims the benefit of U.S. Provisional Application No. 81/227,808, filed Jul. 23, 2009, and priority from Swedish Patent Application 0802153-7, filed Oct. 31, 2008, the entire contents of which is hereby incorporated by reference in this application.

FIELD OF THE INVENTIONS

The present inventions concern methods and devices for therapeutic and cosmetic bone adjustment, and in particular implanted devices, such as but not limited to implanted hydraulic devices, for adjusting the position, length, strength or function of bones in the human or animal body.

BACKGROUND

The art of immobilizing a fractured bone in order to promote healing has been practiced for centuries. Starting from simple splints and sometimes rather unsanitary bandages, the invention of the plaster cast started a new era of orthopaedic medicine. Today, the heavy plaster casts are gradually replaced by lighter fibre glass alternatives. Further, in addition to purely external splints and casts, a variety of internal support structures are widely used. Such support structures include splints affixed directly to the fractured bone, pins and screws used to hold parts of the bone together during healing and to strengthen the site of the fracture. Further examples include plates, perforated scaffolds, intramedullar pins and screws, etc. These can be made of an inert material, such as titan, ceramic, or surgical steel, or made from a material which is resorbed or integrated in the body. Alternatively, the support structure is surgically removed when the fracture is fully healed.

Another group of devices, particularly relevant for the present invention, are mechanical devices which are mainly situated outside the body, but which engage the bones inside the body. The simplest form of such devices is a splint in the shape of a metal rod on the outside of the body, fixed to pins or screws anchored in the bone, and protruding through the skin. More complicated apparatuses include means for adjusting the position of the bones, for example applying tension to the fracture in order to align a complicated fracture, promote healing or to induce bone lengthening, a technique called distraction osteogenesis.

One example of external devices or fixtures for bone lengthening or reshaping is the so called Ilizarov apparatus, originally developed in the 1950s in the Soviet Union, and introduced in Europe in the 1980s. In summary, this is an external fixture attached to the bone through the skin and tissues of the patient, and used in a surgical procedure that can be used to lengthen or reshape bones. Fixtures of this type are often used to treat complex fractures, such as open bone fractures, where conventional treatment techniques cannot always be used. It can also be used to treat infected non-unions of bones not amenable with other techniques. This and similar fixtures are also used for correcting deformities. For more information see e.g. Snela et al 2000.

Another fixture is the Taylor Spatial Frame (TSF), an external fixator sharing a number of components and features of the Ilizarov apparatus, The TSF is a hexapod device consisting of two rings made of aluminium connected together by 6 struts. Each strut can be independently lengthened or shortened. When the apparatus is connected to a bone, by wires or half pins, the attached bone, can be manipulated in 6 axes (anterior/posterior, varus/valgus, lengthen/shorten.) Both angular deformities and translational deformities can be corrected with the TSF. It is used in both adults and children. It is used for the treatment of acute fractures, mal-unions, non uniona and congenital deformities. It can be used on both the upper and lower limbs. Specialised foot rings are also available for the treatment of complex foot deformities.

Once attached to the bone, the deformity is characterised by studying the postoperative x-rays. The angular and translational deformity values are then entered into specialised software along with parameters such as the ring size and initial strut lengths. The software then produces a "prescription" of strut changes that the patient follows. The struts are adjusted every day by the patient. Typically, correction of the bone deformity will take 3 to 4 weeks. Once the deformity has been corrected, the frame is then left on the leg whilst the bone heals, typically this will take 3 to 6 months, depending on the nature and degree of deformity.

Apparatuses of this kind may also be used for the lengthening of bones. This procedure consists of an initial surgery, during which the bone is surgically fractured and the ring apparatus is attached. As the patient recovers, the fractured bone begins to grow together. While the bone is growing, the frame is adjusted by means of turning the nuts, thus increasing the space between two rings. As the rings are connected to opposite sides of the fracture, this adjustment, done daily, moves the slowly healing fracture apart by approximately one millimetre per day. The incremental daily increases result in a considerable lengthening of the limb over time. Once the lengthening phase is complete, the apparatus stays on the limb to facilitate healing. The patient can move about on crutches and pain is lessened. Once healing is complete, a second surgery is necessary to remove the ring apparatus. The result is a limb that is significantly longer. Additional surgery may be necessary, in the case of leg lengthening, to lengthen the Achilles tendon to accommodate the longer bone length. The major advantage of this procedure is that the patient can remain active during the procedure, as the apparatus provides complete support while the bone is recovering. Patient activity and well-being is known to accelerate recovery.

While these external fixtures are minimally invasive (no large incisions are made,) they are not free of complications. Pain is common and can be severe, but is treatable with analgesics. Careful attention to daily cleaning and hygiene is necessary to prevent pin site infection. Other complications include swelling and muscle transfixion. The external fixtures are also bulky, causing inconvenience and attracting unwanted attention in daily life.

There are examples of implantable devices, such as the implantable limb lengthening nail driven by a shape memory alloy disclosed in U.S. Pat. No. 5,415,660. This disclosure concerns an intramedullar nail consisting of an inner cylinder and an outer cylinder enclosing a drive means employing a shape memory alloy. This cylinder is attached to the bone by proximal and distal interlocking bolts, affixed from the outside of the bone, penetrating the bone, e.g. in the area of the epiphysis and the diaphysis, according to the figures in U.S. Pat. No. 5,415,660.

Another example of the background art is the tibial osteotomy fixation device of U.S. Pat. No. 5,827,286, comprising two plate members, telescopically movable in relation to each other, and a ratchet mechanism allowing movement in one direction only. This device is adapted for being attached to the outside of a bone, and affixed with bone screws.

U.S. 2005/0055025 A1 discloses various skeletal implants, connectable to joints or bones, suggesting a mechanism that initially is very rigid and absorbs external chock or stress thus protecting for example a graft or fracture during healing. It is suggested that this mechanism then progressively allows more movement, as the graft or fracture heals.

EP 0 432 253 discloses an intramedullary nail comprising a proximal and a distal end, and a mechanical, pneumatic, hydraulic, electrical or electromagnetic drive for rotating a rod inside said nail, for longitudinally expanding said nail. The nail has securing holes for engaging fastening nails or bolts, to be arranged transversally through the bone and intramedullary nail.

U.S. Pat. No. 5,156,605 concerns medical equipment for use in orthopaedics and traumatology, and is in particular directed to drive systems for a compression-distraction-torsion apparatus. One embodiment concerns an intramedullary device, fully implantable in a patient's bone, and including a motor drive, controller and battery functions, as well as radio frequency or electromagnetic field signals to allow a physician to adjust the rate and rhythm of distraction from outside the body. The device is shown anchored to the bone using nails or bolts penetrating the diaphysis and both end portions of the device.

Another problem associated with known devices is that the tension needs to be adjusted daily, either by the patient themselves, or by medical personnel. When the patient has the responsibility for adjusting the apparatus, there is a risk of poor compliance, due to pain or psychological discomfort.

Further, as there are indications that intermittent loading (Consolo et al., 2006), cyclic distraction and compression (Hente et al., 2004) and even oscillating forces promote osteogenesis and the differentiation of osteoblasts (Gabbay, 2006), the traditional mechanical devices leave room for improvements.

One objective of the present invention is to overcome the problems associated with known external and internal mechanical fixtures and splints.

Another objective is to make available new methods and devices for treatments involving distractive osteogenesis, both for therapeutic and cosmetic purposes.

Further objectives of the invention, as well as advantages associated with embodiments of the invention will become evident to a skilled person upon a closer study of the present description, non-limiting examples, claims and drawings.

SUMMARY

The inventions concern a device for bone adjustment in a mammal, which according to an embodiment comprises two or more anchoring devices for attaching to a bone in said mammal, and an adjustment device for exerting force on said anchoring devices to adjust the distance between or orientation of at least two of said anchoring devices, wherein said anchoring devices and said adjustment device are implanted intramedullary in said mammal and wherein said adjustment device is constructed to postoperatively adjust said distance.

In a device according to said embodiment, the adjustment is the lengthening of a bone, the healing of a fracture, the changing of a bone angle, the reshaping of a bone, the compression of a bone, the torsion of a bone or a combination thereof.

In a device according to any of the embodiments presented herein, said two or more anchoring devices are adapted to engage the bone from the inside of the intramedullar cavity. Preferably said at least two anchoring devices are chosen from a screw, an adhesive, a barb construction, a saw-tooth construction, an expandable element, combinations thereof or other mechanical connecting members.

In a device according to any of the embodiments presented herein, the force exerted by the adjustment device is a longitudinal force, extending the length of the bone.

According to an embodiment, said longitudinal force is directed to the end portions of the medullar cavity.

According to another embodiment, the force exerted by the adjustment device is a longitudinal force, adjusting the angle or curvature of the bone.

According to yet another embodiment, the force exerted by the device applies torque to the bone, adjusting the torsion of the bone along its longitudinal axis.

According to another embodiment, freely combinable with any of the embodiments herein, said device is flexible.

According to another embodiment, the adjustment device comprises a hydraulic device for said bone adjustment, to control the amount of force exerted by the device onto said anchoring devices. Preferably said hydraulic device comprises a cylinder and piston.

According to another embodiment, the hydraulic device comprises a mechanical multi step locking mechanism, locking the hydraulic device in its new position after adjustment. Said mechanical multi step locking mechanism may comprise at least one of a sprint, a elongated structure using the principle of saw teeth, flanges, barbs or a bonnet band, a nut, a gearbox, or a spring loaded locking principle.

According to another embodiment, the hydraulic device comprises hydraulic fluid and a reservoir containing said fluid, adapted to move said fluid to said adjustment device. Preferably said hydraulic fluid is moved from said reservoir to said adjustment device by using a pre-pressurized reservoir or a pump.

According to another embodiment, the hydraulic device comprises a device positioning system such as a fluid volume or flow measurement or any other sensor input to see the position of the adjustment device.

According to another embodiment, the device comprises a control device. Preferably said control device follows a program of incremental changes, set before the device is implanted. Alternatively, said control device follows a program of incremental changes, communicated to the control device after implantation and/or during the treatment. X-ray or ultrasonic follow-up may indicate further treatment, decided by the responsible orthopaedic surgeon.

According to another embodiment, said control device comprises an external con unit and an implantable receiver suitable for wireless communication with said external control unit, having a transmitter located outside the body.

According to another embodiment, said control device controls incremental changes of the adjustment device, communicated to the receiver after implantation and/or during the treatment by using said external control unit.

According to another embodiment, freely combinable with any one of the embodiments presented herein, said hydraulic adjustment device is adapted to being stabilized when the bone adjustment is completed. In this embodiment, the hydraulic adjustment device can be filled with a material which stabilizes the position of the adjustment device and permanents the distance between the anchoring devices.

Preferably said material is chosen from curable foam, a curable gel, a polymer or polymer mixture which solidifies, crosslinks or otherwise attains and retains a stable volume. Alternatively, the hydraulic fluid used in said device is a material chosen from a curable foam, a curable gel, a polymer or polymer mixture which solidifies, crosslinks or otherwise attains and retains a stable volume when the curing, solidification, crosslinking or other reaction is initiated by the user. According to another embodiment, said material chosen from a curable foam a curable gel, a polymer or polymer mixture which solidifies, crosslinks or otherwise attains and retains a stable volume, is added to the device, partially or completely replacing the hydraulic fluid.

When said material solidifies, further movement of the device is prevented, and the device can be left in place if desired. By the verb "fill" .. as in "the device can be filled" is meant that the inside of the device, e.g. the inside of a hydraulic device, such as the hydraulic chamber, piston, bellows or the like, is filled. In a mechanical device, the housing surrounding any movable parts is filled, preventing further movement of said parts.

According to another embodiment, the adjustment device comprises a mechanical device for said bone adjustment. Preferably said adjustment device is operated by an operation device, such as motor.

According to another embodiment, the adjustment device comprises a control device, wherein the operation device is controlled by said control device.

According to another embodiment, the motor comprises a motor or device positioning system such as a tachometer or any other sensor input to see the position of the adjustment device.

According to another embodiment, the mechanical device for said bone adjustment comprises at least one nut and screw.

According to another embodiment, the mechanical device for said bone adjustment comprises at least one gearbox.

According to yet another embodiment, the mechanical device for said bone adjustment comprises a servo mechanism or mechanical amplifier.

According to any one of the embodiments herein, the device is adapted for exerting an intermittent and/or oscillating force. It is here noted that a method for distractive osteogenesis, where the fractured bone is subjected to an intermittent and/or oscillating force using an implanted hydraulic device, is a particularly preferred embodiment of the invention. The device according to the invention is especially suitable for such treatment, as it requires minimal or no manual adjustment, and can exert its force or torque according to a preset program or according to instructions transmitted wirelessly to the device.

According to any one of the embodiments herein, the device comprises a locking device which allows extension of the device but substantially prevents contraction.

Another embodiment of the inventions is a method for bone adjustment in a mammal, wherein a hydraulic or mechanical device according to any one of the above embodiments is used and implanted in the body of said mammal.

According to another embodiment, the device is implanted intramedullary in the body of said mammal, exerting a force to anchoring devices anchored to the inside of said bone.

According to another embodiment of the method, said bone adjustment is the lengthening of a bone, the healing of a fracture, the changing of a bone angle, the reshaping of a bone, the torsion of a bone or a combination thereof.

According to one embodiment, said adjustment is a step in a treatment to correct a limb discrepancy caused by a congenital condition, deformation or previous trauma. For a better understanding of the field, a non-exclusive list of examples is given in Table 1 below. It is conceived that the device and method according to the invention can be applied by a skilled person to any of these, given that the necessary modifications with regard to size, force and location are made. Such modifications however appear to be within the realm of a skilled person without an inventive effort.

Table 1. Examples of Conditions Contemplated as Possible to Treat with a Device and Method According to the Invention Congenital deformities (birth defects), such as congenital short femur; fibular hemimelia (absence of the fibula, which is one of the two bones between the knee and the ankle); hemiatrophy (atrophy of half of the body); and Ollier's disease (also known as multiple endochondromatosis, dyschondroplasia, and endochondromatosis).

Developmental deformities, such as neurofibromatosis (a rare condition which causes overgrowth in one leg); and bow legs, resulting from rickets (rachitis) or secondary arthritis.

Post-traumatic injuries, such as growth plates fractures; malunion or non-union (when bones do not completely join, or join in a faulty position after a fracture); shortening and deformity; and bone defects.

Infections and diseases, such as osteomyelitis (a bone infection, usually caused by bacteria); septic arthritis (infections or bacterial arthritis); and poliomyelitis (a viral disease which may result in the atrophy of muscles, causing permanent deformity).

Reconstruction after removal of tumours.

Short stature, such as achondroplasia (a form of dwarfism where arms and legs are very short, but torso is more normal in size); and constitutional short stature.

According to another embodiment, said adjustment is reshaping or lengthening of a bone involving distraction osteogenesis treatment. Distraction osteogenesis can also be applied to cosmetic lengthening of limbs, although healthy patients are currently often discouraged to undertake such treatments due to the risk of complications, and the cost and suffering involved. It is underlined that the embodiments of the present invention are applicable to both therapeutic and cosmetic uses.

According to yet another embodiment, said adjustment is the reshaping or lengthening of a bone as a step of correcting a congenital deformation.

According to a further embodiment, said adjustment is the reshaping or lengthening of a bone as a step of a cosmetic treatment.

According to any of the above embodiments of the method, reshaping is one of changing the angle or curvature of a bone, changing the torsion of a bone, changing the angle between the diaphysis and the epiphysis, changing the thickness of a bone or a combination thereof.

Another embodiment of the inventions is a method for bone adjustment in a mammal wherein a device is implanted intramedullary in the body of said mammal, wherein said device is a hydraulic device exerting a force to anchoring devices anchored in said bone and a control device which controls the amount of force exerted by the device.

Another embodiment of the inventions is a method for bone adjustment in a mammal wherein a device is implanted intramedullary in the body of said mammal, wherein said device is a mechanical device exerting a force to anchoring devices anchored in said bone and a control device which controls the amount of force exerted by the device.

In any of the above methods, said control device follows a program of incremental changes, set before the device is implanted. Alternatively, said control device follows a program of incremental changes, communicated to the control device after implantation and/or during the treatment.

According to any of the embodiments of the method, said device is stabilized when the treatment is completed. Preferably said device is stabilized by filling the device with a material which stabilizes the position of the adjustment device and permanents the distance between the anchoring devices. In this method said material is chosen from a curable foam, a curable gel, a polymer or polymer mixture which solidifies, crosslinks or otherwise attains and retains a stable volume.

Alternatively, the device is a hydraulic device and the hydraulic fluid is a material chosen from a curable foam, a curable gel, a polymer or polymer mixture which solidifies, crosslinks or otherwise attains and retains a stable volume when the curing, solidification, crosslinking or other reaction is initiated by the user.

According to another embodiment, the device is a hydraulic device and a material chosen from a curable foam, a curable gel, a polymer or polymer mixture which solidifies, crosslinks or otherwise attains and retains a stable volume, is added to said device, partially or completely replacing the hydraulic fluid.

Another embodiment of the inventions is a method for distractive osteogenesis where the fractured bone is subjected to an intermittent and/or oscillating force using an implanted hydraulic or mechanical device.

Another embodiment of the inventions is a method for treating a bone dysfunction of a mammal patient by providing a device for bone adjustment comprising at least two anchoring devices according to any one of embodiments of a device according to the inventions, the method comprising the steps of
  i. inserting a needle or tube-like instrument into a cavity of said mammal patient;
  ii. inflating said cavity by introducing a fluid through said needle or tube-like instrument and thereby expanding said cavity;
  iii. placing at least two laparoscopic trocars in said cavity;
  iv. inserting a camera through one of said laparoscopic trocars into said cavity;
  v. inserting at least one dissecting tool through one of said a east two laparoscopic trocars;
  vi. dissecting an area of the dysfunctional bone;
  vii. placing the device for bone adjustment and anchoring devices in the medullar cavity of said bone;
  viii. anchoring said anchoring devices in contact with said bone;
  ix. closing the mammal body preferably in layers; and
  x. non-invasively adjusting said bone postoperatively.

Another embodiment of the inventions is a method of treating a bone dysfunction of a mammal patient by providing a device for bone adjustment comprising at least two anchoring devices according to any one the embodiments of the device according to the inventions, comprising the steps of:
  i. cutting the skin of said human patient;
  ii. dissecting an area of the dysfunctional bone;
  iii. placing the device in the medullar cavity of said bone;
  iv. anchoring said anchoring devices in contact with said bone;
  v. closing the mammal body preferably in layers; and
  vi. non-invasively adjusting said bone postoperatively.

According to a further embodiment, the method of treating a mammal patient further comprises the step of withdrawing the instruments.

According to a further embodiment, the method of treating a mammal patient further comprises the step of closing the skin using sutures or staples.

According to a further embodiment, the step of dissecting includes dissecting an area of the arm or leg comprising, dissecting an area of at least one of the following bones; clavicula, scapula, humerus, radius, ulna, pelvic bone, femur, tibia, fibula or calcaneus.

According to a further embodiment, the step of dissecting includes dissecting, an area of the arm or leg comprising, dissecting an area at least one of the following joints; shoulder, elbow, hip, knee, hand and foot.

According to a further embodiment of the method, an opening into the medullar cavity is made by drilling.

Another embodiment of the inventions relates to a system comprising an apparatus or device according to any one of the embodiments presented herein.

According to a further embodiment, said system further comprises at least one switch implantable in the patient for manually and non-invasively controlling the apparatus.

According to a further embodiment, said system further comprises a hydraulic device having an implantable hydraulic reservoir, which is hydraulically connected to the apparatus, wherein the apparatus is adapted to be non-invasively regulated by manually pressing the hydraulic reservoir.

According to a further embodiment, said system further comprises a wireless remote control for non-invasively controlling the apparatus.

According to an embodiment, said wireless remote control comprises at least one external signal transmitter and/or receiver, further comprising an internal signal receiver and/or transmitter implantable in the patient for receiving signals transmitted by the external signal transmitter or transmitting signals to the external signal receiver.

According to an embodiment, said wireless, remote control transmits at east one wireless control signal for controlling the apparatus.

According to an embodiment, said wireless control signal comprises a frequency, amplitude, or phase modulated signal or a combination thereof.

According to an embodiment, said wireless remote control transmits an electromagnetic carrier wave signal for carrying the control signal.

According to yet another embodiment, said system further comprises a wireless energy-transmission device for non-invasively energizing implantable energy consuming components of the apparatus with wireless energy.

According to an embodiment, said wireless energy comprises a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal.

According to an embodiment, said wireless energy comprises one of the following: an electric field, a magnetic field, a combined electric and magnetic field.

According to an embodiment, said control signal comprises one of the following: an electric field, a magnetic field, a combined electric and magnetic field.

According to a further embodiment, said the signal comprises an analogue signal, a digital signal, or a combination of an analogue and digital signal.

According to yet another embodiment, said system further comprises an implantable internal energy source for powering implantable energy consuming components of the apparatus.

According to yet another embodiment, said system further comprises an external energy source for transferring energy in a wireless mode, wherein the internal energy source is chargeable by the energy transferred in the wireless mode.

According to yet another embodiment, said system further comprises a sensor or measuring device sensing or measuring a functional parameter correlated to the transfer of energy for charging the internal energy source, and a feedback device for sending feedback information from inside the patient's body to the outside thereof, the feedback information being related to the functional parameter sensed by the sensor or measured by the measuring device.

According to yet another embodiment, said system further comprises a feedback device for sending feedback information from inside the patient's body to the outside thereof, the feedback information being related to at least one of a physical parameter of the patient and a functional parameter related to the apparatus.

According to yet another embodiment, said system further comprises a sensor and/or a measuring device and an implantable internal control unit for controlling the apparatus in response to information being related to at least one of a physical parameter of the patient sensed by the sensor or measured by the measuring device and a functional parameter related to the apparatus sensed by the sensor or measured by the measuring device.

According to another embodiment, said physical parameter is a pressure or a motility movement.

According to yet another embodiment, said system further comprises an external data communicator and an implantable internal data communicator communicating with the external data communicator, wherein the internal communicator feeds data related to the apparatus or the patient to the external data communicator and/or the external data communicator feeds data to the internal data communicator.

According to yet another embodiment, said system further comprises a motor or a pump for operating the apparatus.

According to yet another embodiment, said system further comprises a hydraulic operation device for operating the apparatus.

According to yet another embodiment, said system further comprises an operation device for operating the apparatus, wherein the operation device comprises a servo designed to decrease the force needed for the operation device to operate the apparatus instead the operation device acting a longer way, increasing the time for a determined action.

According to yet another embodiment, said system further comprises an operation device for operating the apparatus, wherein the wireless energy is used in its wireless state to directly power the operation device to create kinetic energy for the operation of the apparatus, as the wireless energy is being transmitted by the energy-transmission device.

According to yet another embodiment, said system further comprises an energy-transforming device for transforming the wireless energy transmitted by the energy-transmission device from a first form into a second form of energy.

According to an embodiment, said energy-transforming device directly powers implantable energy consuming components of the apparatus with the second form energy, as the energy-transforming device transforms the first form energy transmitted by the energy-transmission device into the second form energy.

According to an embodiment, said second form energy comprises at least one of a direct current, pulsating direct current and an alternating current.

According to yet another embodiment, said system further comprises an implantable accumulator, wherein the second form energy is used at least partly to charge the accumulator.

According to an embodiment, said energy of the first or second form comprises at least one of magnetic energy, kinetic energy, sound energy, chemical energy, radiant energy, electromagnetic energy, photo energy, nuclear energy thermal energy, non-magnetic energy, non-kinetic energy, non-chemical energy, non-sonic energy, non-nuclear energy and non-thermal energy.

According to yet another embodiment, said system further comprises implantable electrical components including at least one voltage level guard and/or at least one constant current guard.

According to yet another embodiment, said system further comprises a control device for controlling the transmission of wireless energy from the energy-transmission device, and an implantable internal energy receiver for receiving the transmitted wireless energy, the internal energy receiver being connected to implantable energy consuming components of the apparatus for directly or indirectly supplying received energy thereto, the system further comprising a determination device adapted to determine an energy balance between the energy received by the internal energy receiver and the energy used for the implantable energy consuming components of the apparatus, wherein the control device controls the transmission of wireless energy from the external energy-transmission device, based on the energy balance determined by the determination device.

According to an embodiment, said determination device is adapted to detect a change in the energy balance, and the control device controls the transmission of wireless energy based on the detected energy balance change.

According to a further embodiment, the determination device is adapted to detect a difference between energy received by the internal energy receiver and energy used for the implantable energy consuming components of the apparatus, and the control device controls the transmission of wireless energy based on the detected energy difference.

According to a further embodiment, the energy-transmission device comprises a coil placed externally to the human body, further comprising an implantable energy receiver to be placed internally in the human body and an electric circuit connected to power the external coil with electrical pulses to transmit the wireless energy, the electrical pulses having leading and trailing edges, the electric circuit adapted to vary first time intervals between successive leading and trailing edges and/or second time intervals between successive trailing and leading edges of the electrical pulses to vary the power of the transmitted wireless energy, the energy receiver receiving the transmitted wireless energy having a varied power.

According to a further embodiment, the electric circuit is adapted to deliver the electrical pulses to remain unchanged except varying the first and/or second time intervals.

According to a further embodiment, the electric circuit has a time constant and is adapted to vary the first and second time intervals only in the range of the first time constant, so that when the lengths of the first and/or second time intervals are varied the transmitted power over the coil is varied.

According to a further embodiment, the system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil, wherein the external second coil of the energy transmitter transmits wireless energy which is received by the first coil of the energy receiver, the system further comprising a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off.

According to a further embodiment, the system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil, wherein the external second coil of the energy transmitter transmits wireless energy which is received by the first coil of the energy receiver, the system further comprising a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factors between the first and second coils.

According to an embodiment, the transmitted energy may be regulated depending on the obtained coupling factor.

According to a further embodiment, said external second coil is adapted to be moved in relation to the internal first coil to establish the optimal placement of the second coil, in which the coupling factor is maximized.

According to a further embodiment, said external second coil is adapted to calibrate the amount of transferred energy to achieve the feedback information in the determination device, before the coupling factor is maximized.

According to yet another embodiment, the mechanical device comprises a mechanical multi step locking mechanism, locking the mechanical device in its new position after adjustment.

According to yet another embodiment, the mechanical multi step locking mechanism comprises at least one of a sprint, a elongated structure using the principle of saw teeth, flanges, barbs or a bonnet band, a nut, a gearbox, or a spring loaded locking principle.

According to a further embodiment of the system, the device comprises a control device.

According to another embodiment, said control device follows a program of incremental changes, set before the device is implanted.

According to another embodiment, said control device follows a program of incremental changes, communicated to the control device after implantation and/or during the treatment.

According to another embodiment, said control device comprises an external control unit and an implantable receiver suitable for wireless communication with said external control unit, having a transmitter located outside the body.

According to another embodiment, said control device controls incremental changes of the adjustment device, communicated to the receiver after implantation and/or during the treatment by using said external control unit.

According to a preferred embodiment, said device is flexible to allow introduction into the medullar cavity. Alternatively or in combination therewith, said device is at least partly elastic. Alternatively or in combination therewith, said device comprises a spring. Alternatively or in combination therewith, said device is adapted to regain its shape after having been bent.

According to another embodiment, freely combinable with the other embodiments presented herein, the anchoring device comprises a thread for engaging and stabilizing the anchoring device in relation to the bone.

According to a further embodiment, the anchoring device comprises an expandable part expanding at least partially perpendicular to the longitudinal extension of the elongated device for engaging and stabilizing the anchoring device in relation to the bone.

According to a further embodiment, the adjustment device is adapted to comprise torsion of a bone. Alternatively, or in combination, said adjustment device is adapted to change the angle of a bone.

According to a further embodiment, said adjustment device comprises at least two parts, wherein the parts are adapted to rotate in relation to each other. Preferably said relative rotation is anchored by said at least two anchoring devices.

According to another embodiment, freely combinable with the other embodiments presented herein, said adjustment device is adapted to change the angle of a bone.

According to further embodiment, freely combinable with the other embodiments presented herein, said adjustment device comprises at least two parts, wherein the parts are adapted to be positioned at an angle in relation to each other.

According to a further embodiment, said two or more anchoring devices are adapted to engage and carry weight purely on the inside of the bone.

According to yet another embodiment, said two or more anchoring devices are adapted to engage with and carry weight to the bone without penetrating to the outside of the bone.

According to yet another embodiment, said two or more anchoring devices are adapted to engage and carry weight purely on the outside of the bone.

According to another embodiment, freely combinable with any embodiment presented herein, said device comprises a sensor directly or indirectly sensing the position of the adjustment device.

According to a further embodiment, the device comprises a feedback transmitter adapted to transmit information received directly or indirectly from said sensor out from the human body, said transmitted information adapted to be received by a external control unit and relating to the position of the adjustment device.

According to another embodiment of the device, said operation device is a motor operated as a three-phase motor. Alternatively, said operation device is a motor operated as a two- or more phase motor.

According to another embodiment, freely combinable with any embodiment presented herein, said device comprises a gearbox connected to the motor, a motor package, wherein the outgoing speed from the motor package is lower than the speed by said motor alone, accomplished by said gearbox.

According to another embodiment, freely combinable with any embodiment presented herein, said device comprises an electrical speed controller connected to the motor, a motor package, wherein the outgoing speed of the motor in said motor package is decreased by said electrical speed controller.

According to any of the above embodiments, the motor is a rotational motor and the outgoing speed of the motor package is decreased to less than 100 turns per second, alternatively decreased to less than 10 turns per second, alternatively to less than 1 turn per second, or alternatively to less than 0.1 turn per second, or alternatively to less than 0.01 turn per second, or alternatively to less than 0.001 turn per second.

According to another embodiment, freely combinable with any embodiment presented herein, said device comprises an electrical speed controller connected to the motor, a motor package, wherein the outgoing speed of the motor of said motor package is controlled by said electrical speed controller.

According to any of the above embodiments, the motor is a linear motor and the outgoing speed of the motor package is less than 1 mm per second, alternatively less than 0.1 mm per second, or alternatively less than 0.01 mm per second, or alternatively less than 0.001 mm per second, or alternatively less than 0.0001 mm per second, or less than 0.00001 mm per second.

One advantage of the device and method according to the inventions is that the need for manual adjustment of the device is removed. In a traditional, external apparatus, the distance of the elements is adjusted manually, in increments. It is conceived that each incremental adjustment is associated with pain, whereas an automatic, constant adjustment may be better tolerated.

Another advantage is that the implanted device can exert an oscillating or intermittent force without the need for manual adjustments, or the need of connecting the patient to an external apparatus.

Yet another advantage is that the number and size of visible elements outside the body is minimised. This is an important aesthetic and practical improvement, which also has social and psychological benefits, as the patient becomes less exposed and attracts less attention. A provision of an implanted device may also help the patient to feel intact and healthier, thus promoting a positive mental attitude and promoting healing.

It should be noted that the above embodiments, and features appearing in the individual embodiments, are freely combinable.

SHORT DESCRIPTION OF THE DRAWINGS

The invention will be disclosed in further detail in the following description examples and claims, with reference to the attached drawings in which FIG. 1 (Prior art) shows an intramedullar device or internal autodistractor according to U.S. Pat. No. 5,156,605, inserted into the intramedullar cavity of a femur through an opening A in the epiphysis. The device is anchored by a pair of interlocking screws B at the top of the assembly, and by a pair of interlocking bolts C which will pass through the bottom of the assembly, and secure it to the femur.

FIG. 2 (Prior art) shows an intramedullar pin or medullar nail according to EP 432 253 B1, also published as WO 91/00065, having securing holes E and D and a mechanical, pneumatic, hydraulic, electrical or electromagnetic drive for rotating the rod for the longitudinal displacement of an inner portion thereof.

FIG. 3 (Prior art) schematically shows an external fixator (1) of the type frequently referred to as an Ilizarov apparatus, here consisting of two rings (2, 3) having pins (4) attached to and stabilizing the tibia or fibula in the lower leg (5) of a patient. The distance between the rings (2, 3) of the fixator (1) can be adjusted by manually turning threaded cylinders (6, 7, 8) on struts connecting the rings.

FIG. 4 shows one embodiment of the invention where two implanted devices are arranged to a bone.

FIG. 5 shows a detailed view of a device for bone adjustment according to an embodiment of the invention.

Figure 6:
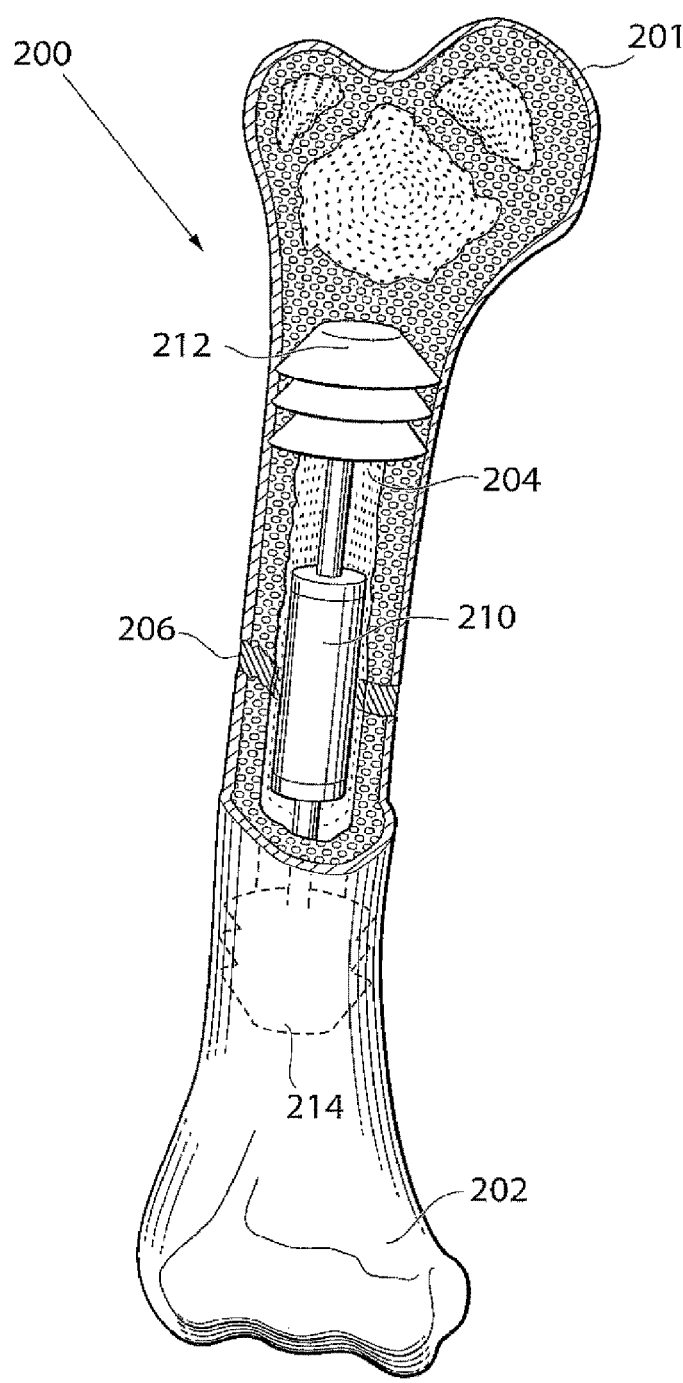

FIG. 6 schematically shows a device according to an embodiment of the inventions, implanted into the medullar cavity of a bone.

FIGS. 7a and 7b show detail views of devices according to embodiments of the invention.

FIGS. 8a-8c shows in detail 8a a schematic lateral view of the human spine, columna vertebralis (500) and illustrates in the partial views 8b and 8c how devices according to embodiments of the invention can be applied.

Figure 9:
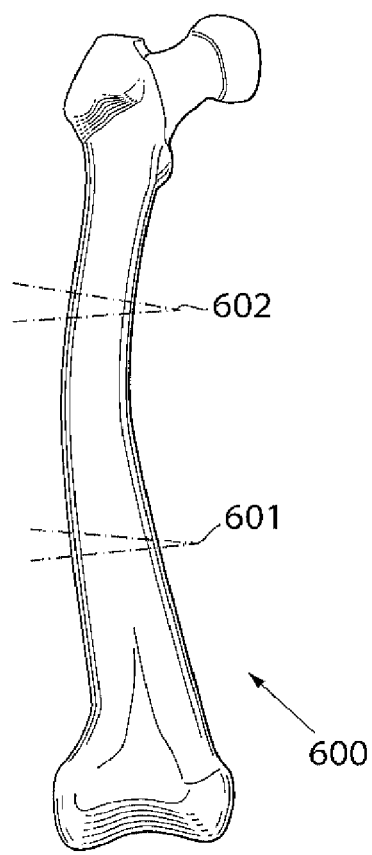
Figure 9:
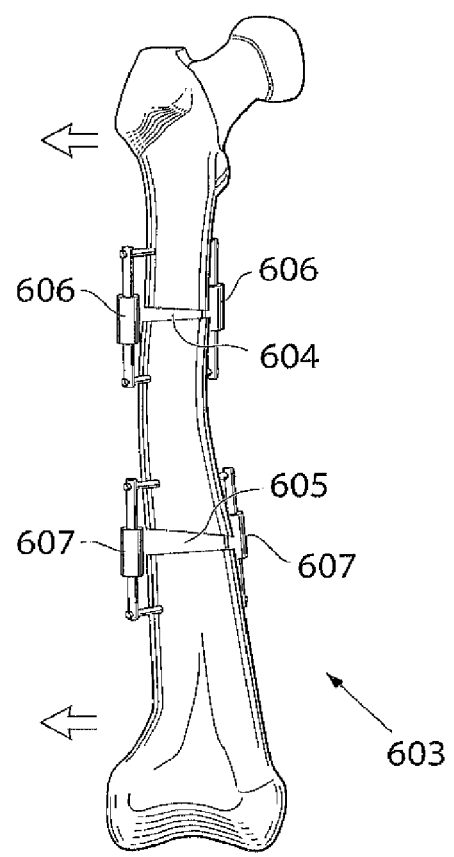
Figure 9:
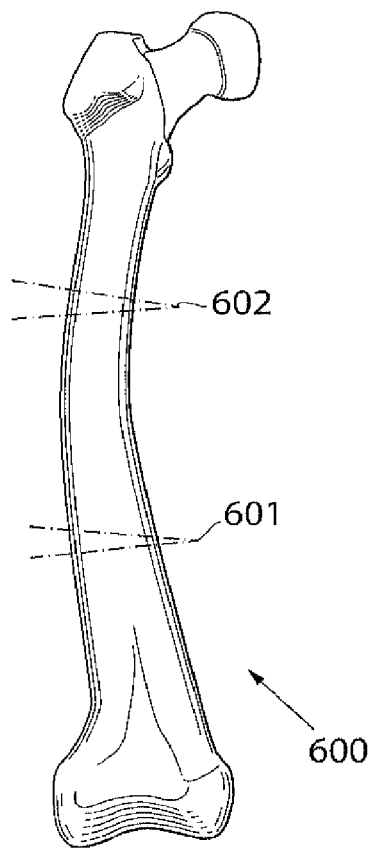
Figure 9:
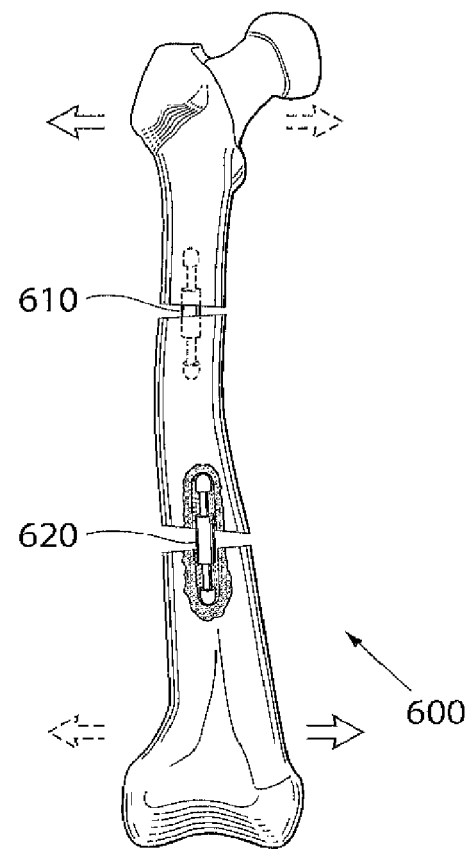

FIGS. 9a and 9b illustrate the straightening of a bone, or how the curvature of a bone can be adjusted, using devices according to embodiments of the invention.

FIGS. 9c and 9d show how the curvature of a bone, here a femur, can be adjusted using intramedullar devices according to embodiments of the invention.

FIGS. 9e and 9f illustrate how an intramedullar device can be used to adjust the torsion of a bone, here illustrated as the femur.

FIGS. 10a and 10b show schematically detail views of two devices according to embodiments of the invention, said devices including a mechanical multi step locking device.

Figure 11:
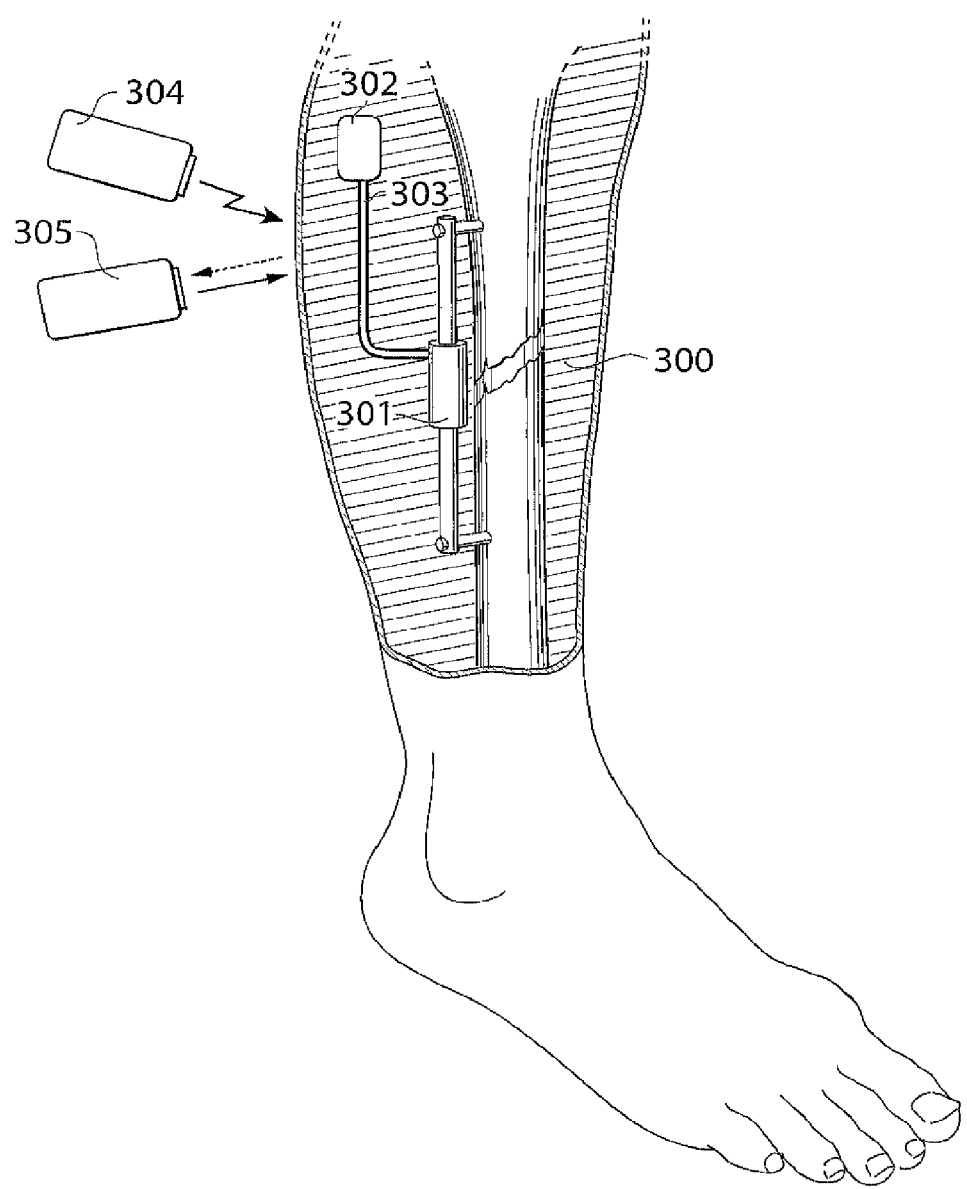
Figure 13A:
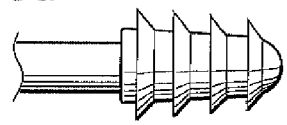
Figure 13B:
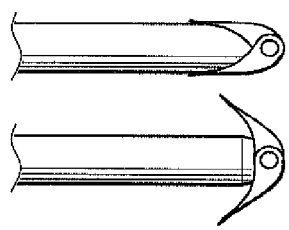
Figure 13C:
Figure 13D:
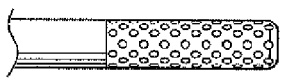
Figure 13E:
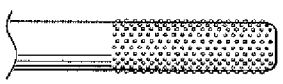

FIG. 11 schematically illustrates a system for bone adjustment according to one embodiment of the invention, described in closer detail in the detailed description.

FIGS. 12a-12d schematically shows the insertion of a flexible device according to an embodiment of the invention.

FIGS. 13a-13e illustrate different non-limiting examples of the construction of the end-portions of the fastening means or anchoring devices according to embodiments of the invention.

FIGS. 14-28 schematically show various embodiments of the system for wirelessly powering an apparatus, for example, but not limited to, those shown in FIG. 4, 11, 12 and FIG. 38.

Figure 29:
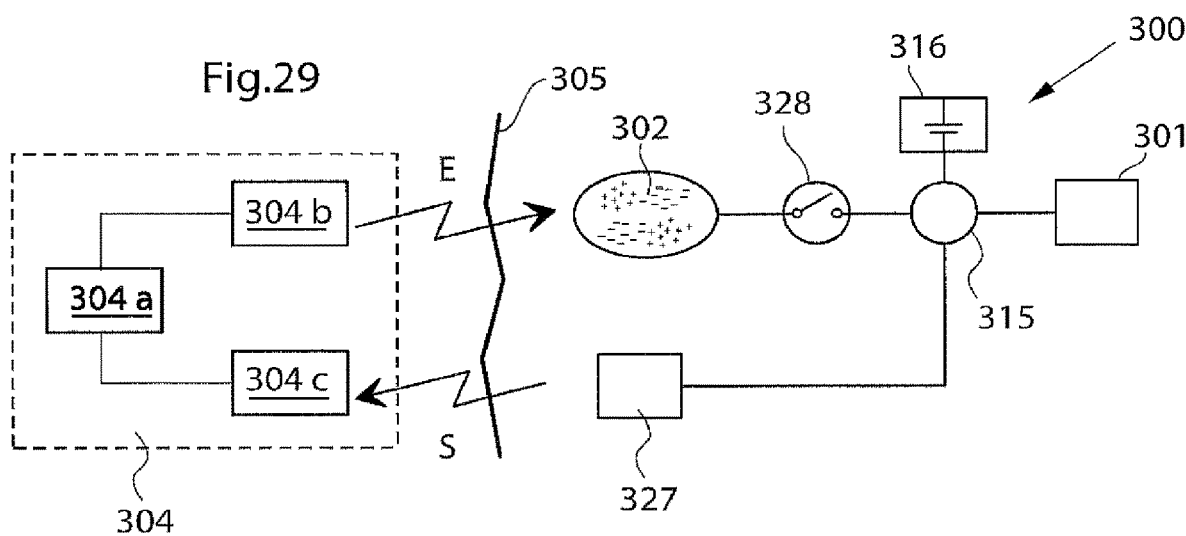

FIG. 29 is a schematic block diagram illustrating an arrangement for supplying an accurate amount of energy used for the operation of the apparatus shown in FIG. 11.

Figure 30:
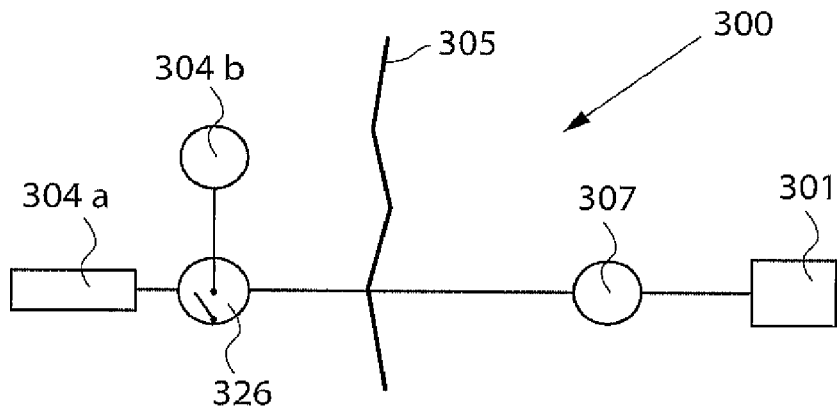

FIG. 30 schematically shows an embodiment of the system, in which the apparatus is operated with wire-bound energy.

Figure 31:
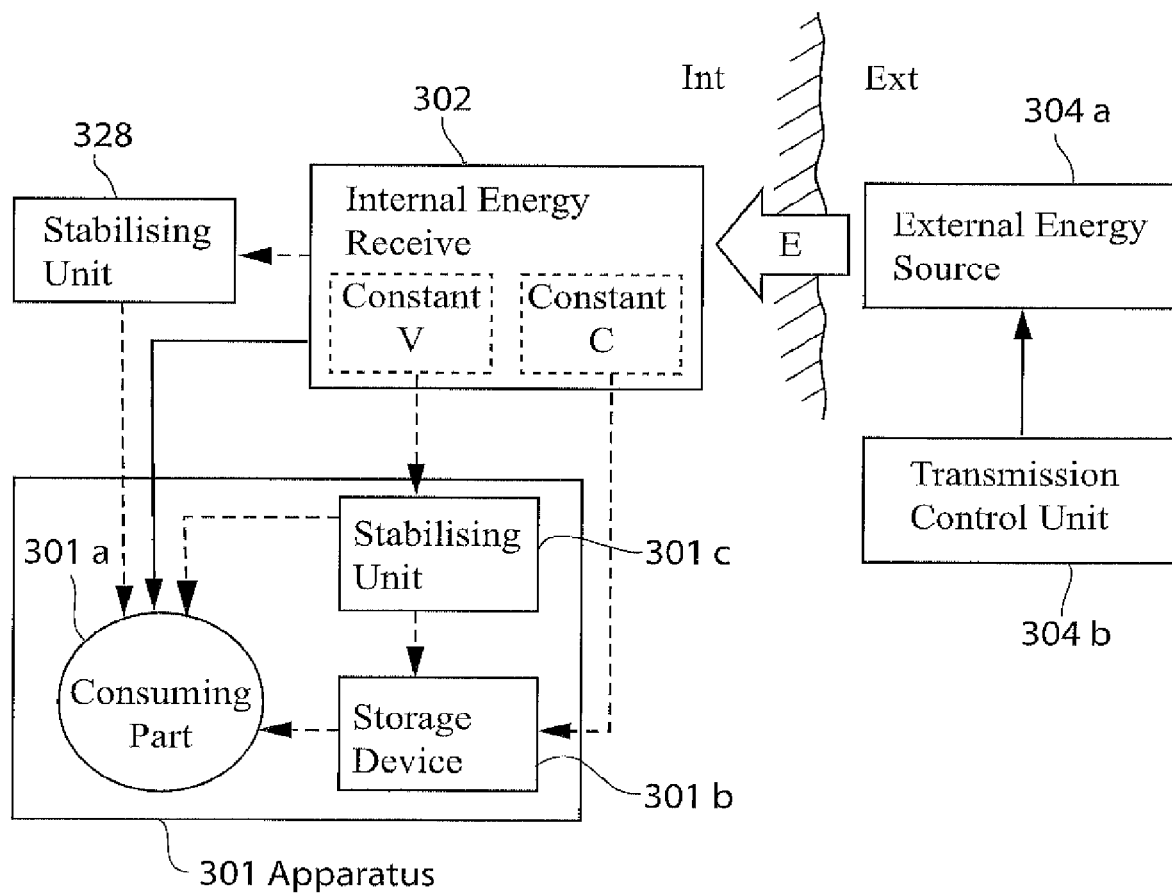

FIG. 31 is a more detailed block diagram of an arrangement for controlling the transmission of wireless energy used for the operation of the apparatus shown in FIG. 11.

Figure 27:
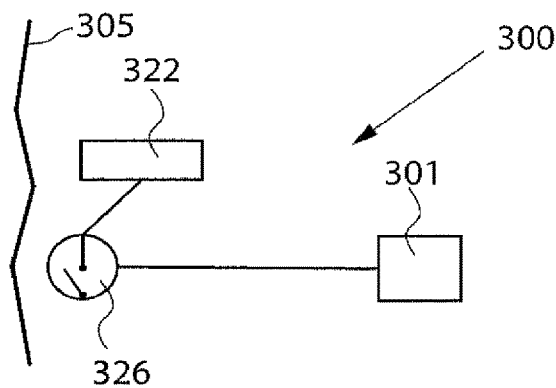
Figure 32:
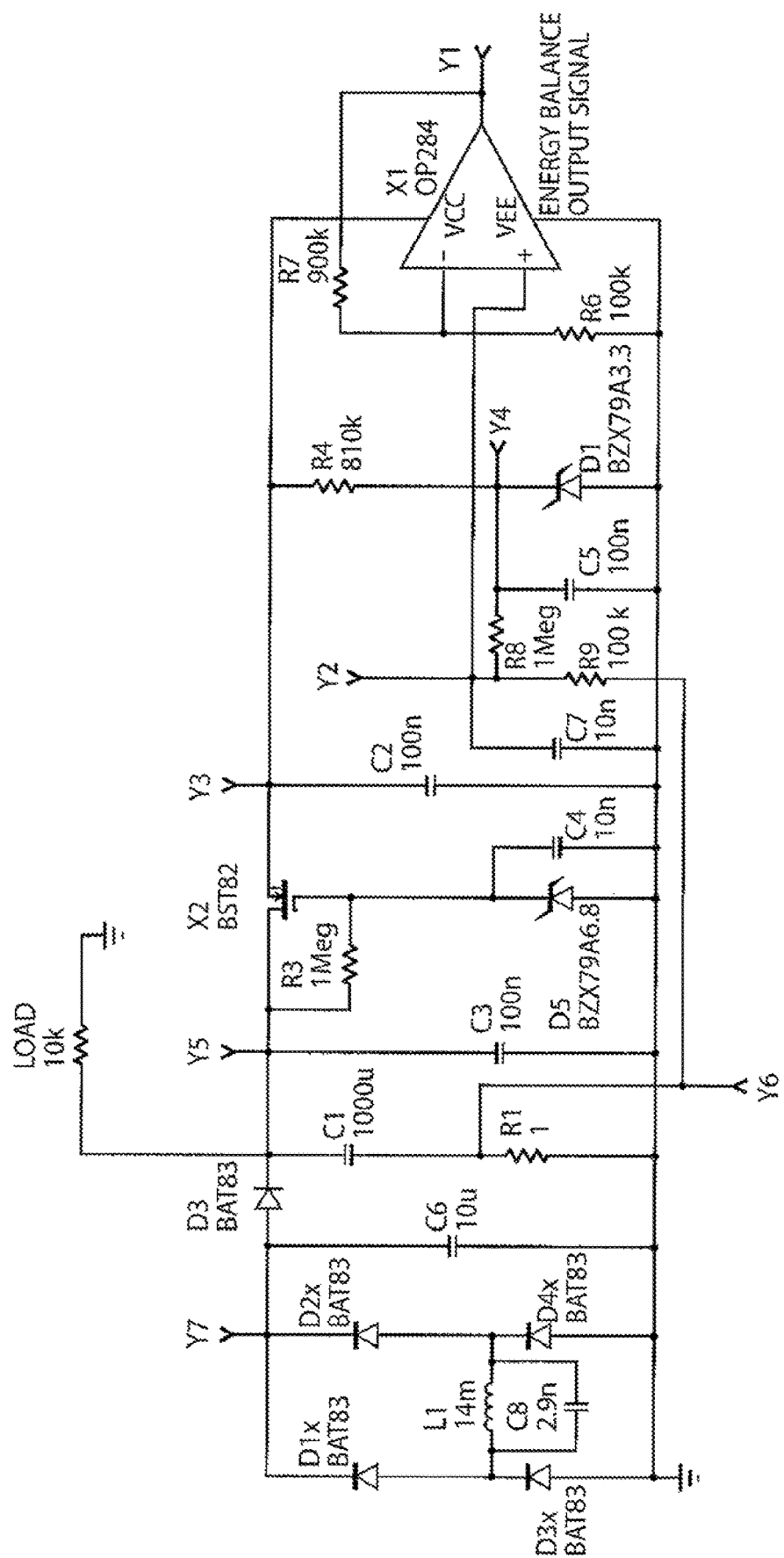

FIG. 32 shows a circuit drawing for the arrangement shown in FIG. 27, according to a possible implementation example.

Figure 33:
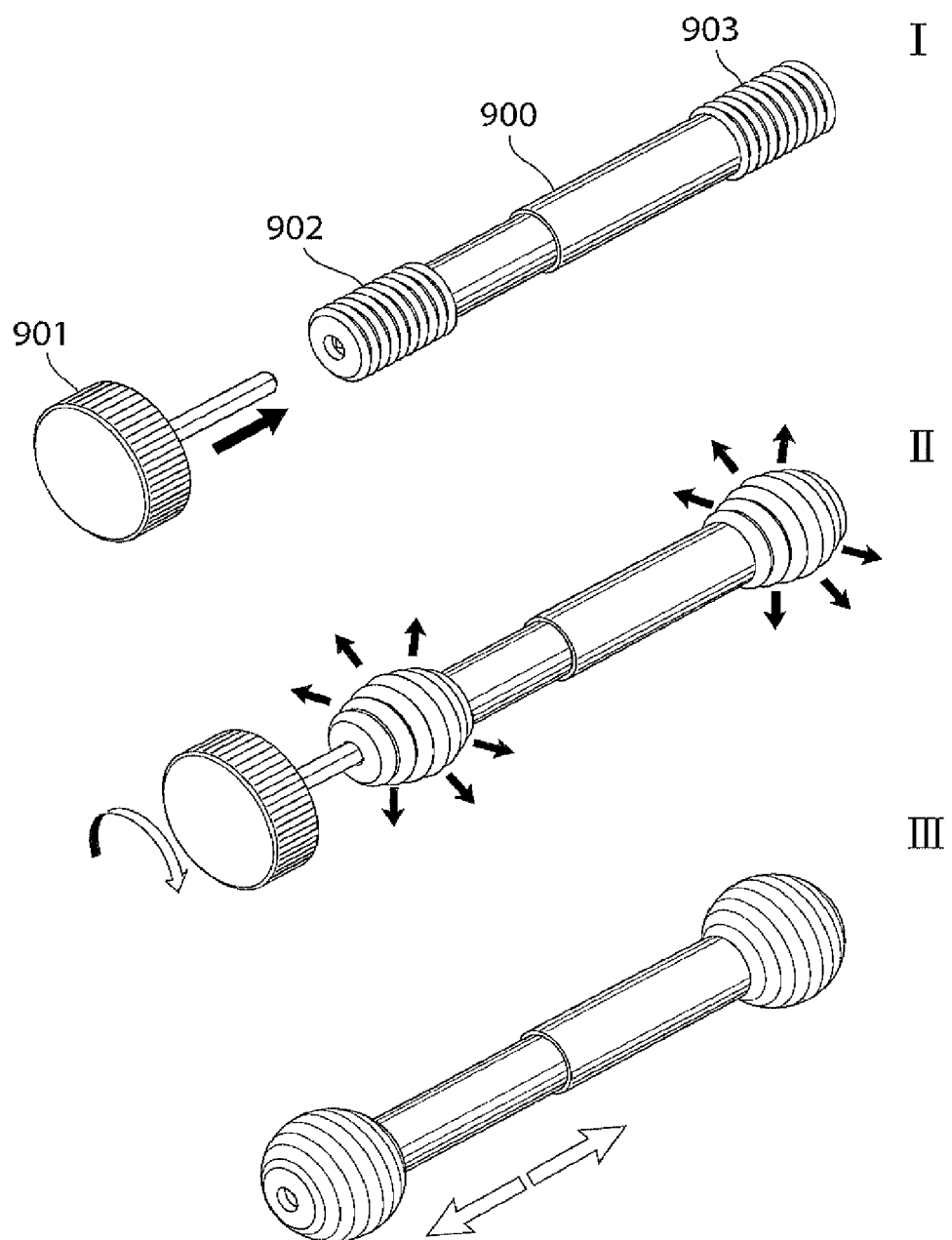

FIG. 33 illustrates anchoring devices according to an embodiment of the invention.

Figure 34:
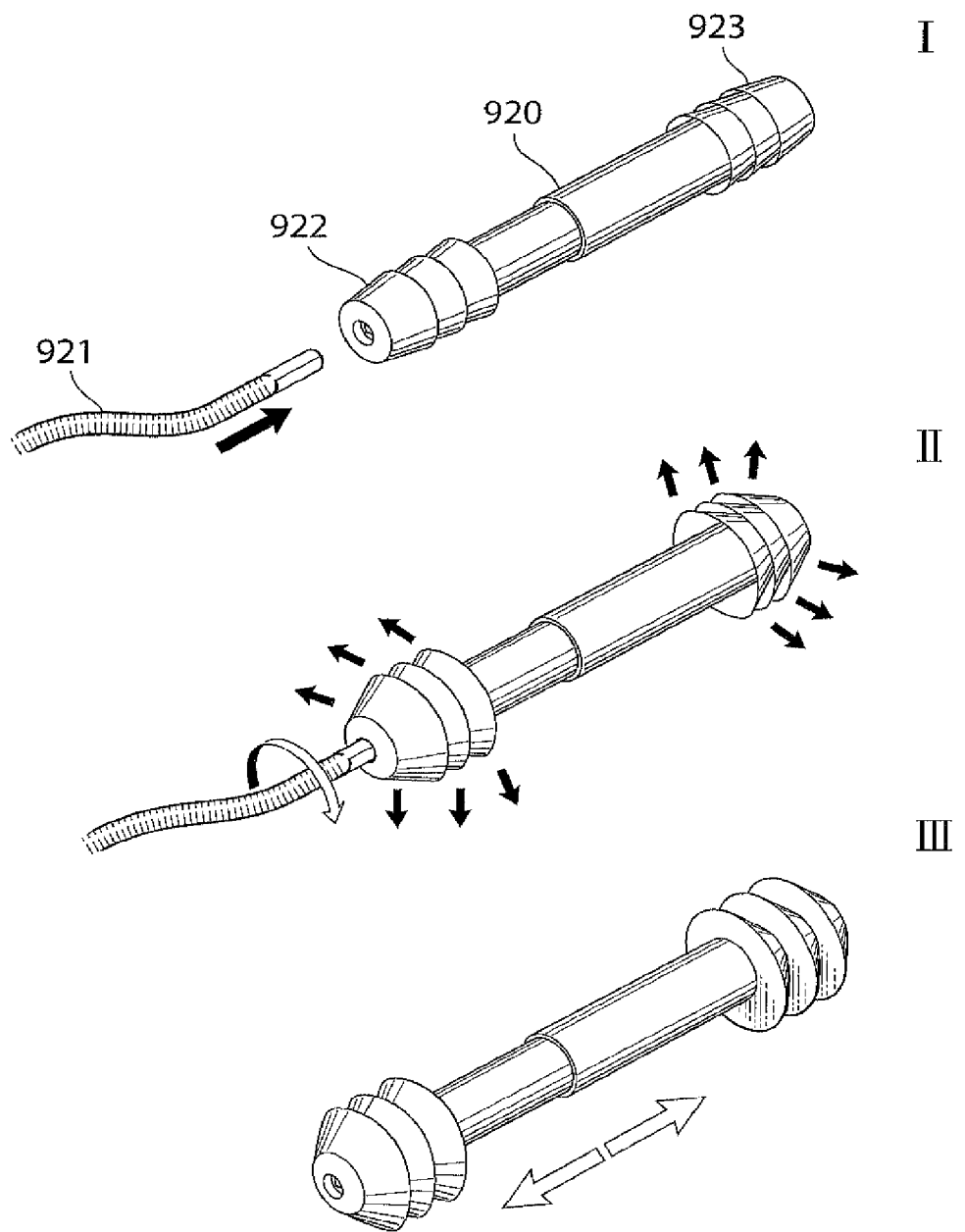

FIG. 34 illustrates anchoring devices according to another embodiment of the invention.

Figure 35:
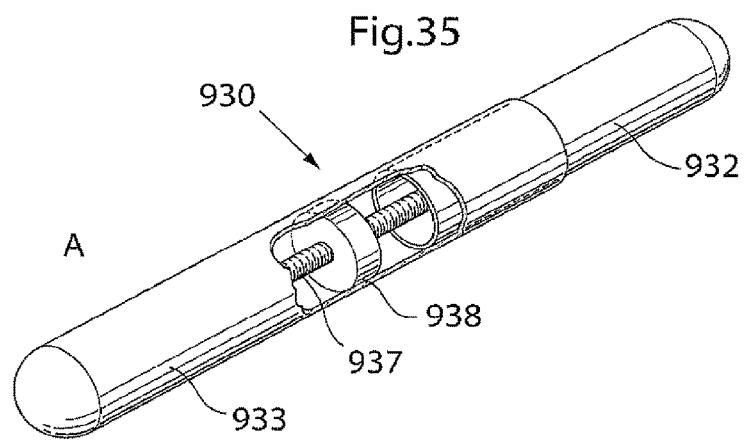

FIG. 35 illustrates an embodiment of the device, comprising two telescopically arranged parts, housing a longitudinal threaded central shaft or axis and a motor or gear arrangement acting thereon, transforming rotational force into longitudinal force and extension or contraction of the device.

Figure 36:
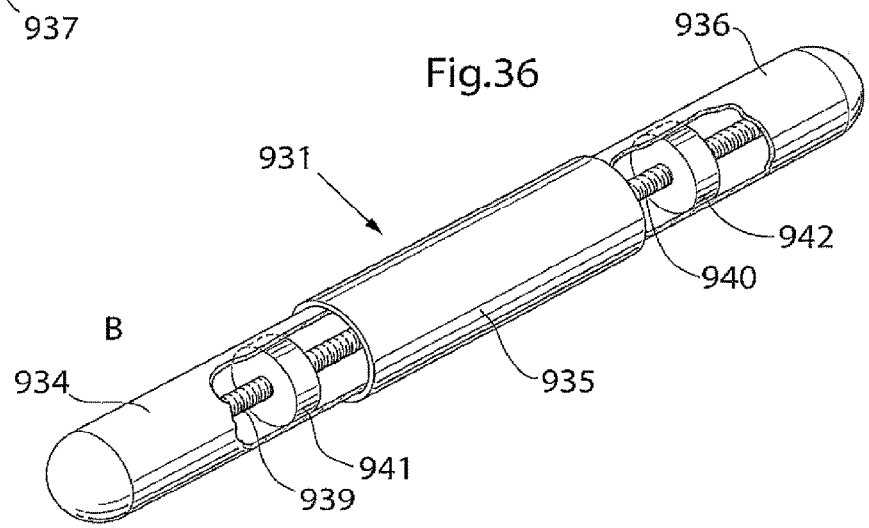

FIG. 36 shows a related embodiment where the device comprises three main parts, a central section, and two telescopically arranged end sections, each connected to a longitudinal threaded central shaft or axis through a motor or gear arrangement.

Figure 37:
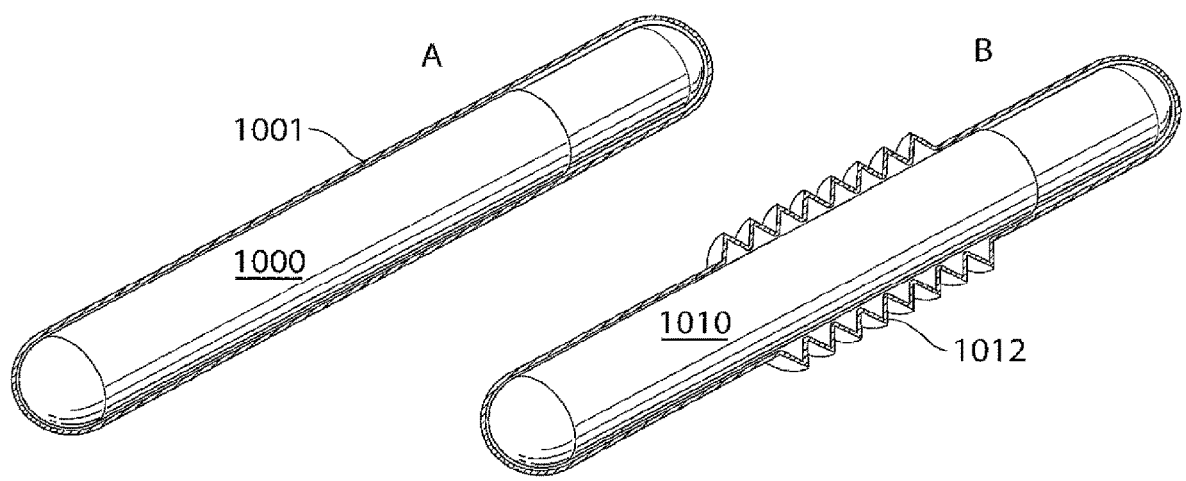

FIG. 37A and B show embodiments where a device for bone adjustment according to the present invention is enclosed in a flexible, elastic or expandable outer cover.

Fig,. 38 illustrates an implanted device according to the invention, where the anchoring devices engage the bone from the inside of the medullar cavity.

Figure 39:
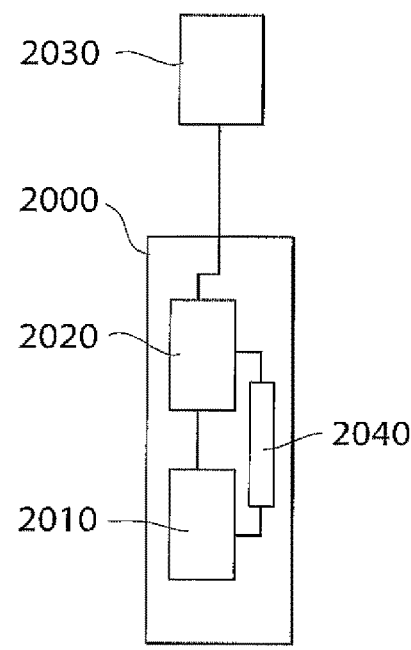

FIG. 39 shows schematically an embodiment of a device comprising a motor, a gear box and a speed controller.

Figure 40:
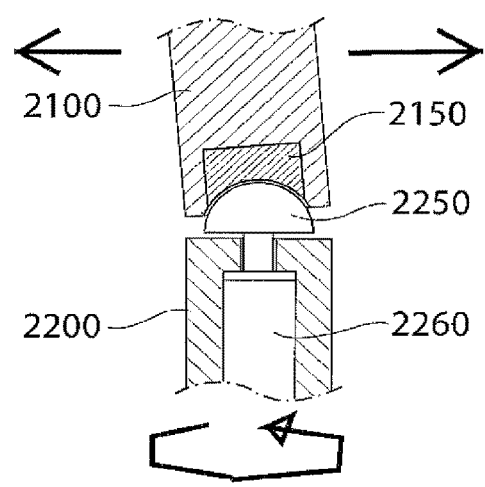

FIG. 40 schematically shows an embodiment where the implanted adjustment device comprises at least two parts, wherein the parts are adapted to be positioned at an angle in relation to each other, and/or rotated in relation to each other.

DETAILED DESCRIPTION

Before the present invention is described, it is to be understood that the terminology employed herein is used for the purpose of describing particular embodiments only and is not intended to be limiting, since the scope of the present invention will be limited only by the appended claims and equivalents thereof.

It must be noted that, as used in this specification and the appended claims, the singular forms "a," "an," and "the" include plural referents unless the context clearly dictates otherwise.

Also, the term "about" is used to indicate a deviation of +/−2% of the given value, preferably +/−5%, and most preferably +/−10% of the numeric values, where applicable.

The term "animal" encompasses all mammals and in particular humans. Similarly the terms "treatment", "therapy", and "therapeutic use" encompass both human and animal or veterinary applications.

The term "extension device" comprises any device which is capable of longitudinal movement and in particular capable of exerting a force longitudinally between two or more points. An extension device can be a hydraulic device, an electronic device, a mechanical device, or a combination of two or more of the previous.

The term "hydraulic device" comprises any device wherein the energy that brings about the longitudinal force is transmitted by a hydraulic fluid acting on elements in the device. Examples of such elements include, but are not limited to hydraulic cylinders, hydraulically inflatable tubes balloons, bellows and the like.

The term "implanted" indicates that a device or an element of a device is introduced permanently or temporarily into a human or animal body. An implanted device can be contained within the human or animal body in its entirety, or only partially, for example by being accessible through a port or other interface in the skin of said human or animal. An implanted device can be enclosed in a human or animal body in its entirety, and communicate wirelessly with an external apparatus for transmitting and receiving signals, for example transmitting measurement data and receiving control signals, and for receiving energy.

The inventions also concern a device for bone adjustment in a mammal, which according to an embodiment comprises two or more anchoring devices for attaching to a bone in said mammal, and an adjustment device for exerting force on said anchoring devices to adjust the distance between or orientation of at least two of said anchoring devices, wherein said anchoring devices and said adjustment device are implanted in said mammal and wherein said adjustment device is constructed to postoperatively adjust said distance.

This is illustrated schematically in FIG. 4 where a fractured tibia (10) having a fracture zone (20) is shown, supported by two devices (40, 50) according to the invention, both devices being attached to anchoring devices (31 32, 33, 34) attached to the bone.

FIG. 5 shows a detailed view where an extension device, here schematically shown as a hydraulic device (80) having two actuators (91, 92) attached to two anchoring devices (101, 102) which can be conventional pins or screws, suitable for inserting in bone. The hydraulic device is in fluid contact through a tube (110) to a hydraulic power unit (120) supplying pressurized hydraulic fluid, which in turn communicates with a control unit (130). Optionally, said control element also supplies the hydraulic power unit with energy. The hydraulic power unit may comprise a reservoir and a pump or a hydrophore type of pre-pressurized expansion reservoir or any other hydraulic solution. The control unit, energy source, reservoir, pump or motor may all be implanted separate or together in any combination.

The power unit 120 can further be connected to or comprise a hydraulic pump 121 associated with a reservoir 122 containing of a fluid used to regulate the pressure of the device 80. The pump is thus adapted to pump the hydraulic fluid in or out from the device 80 in order to adjust the pressure in the device and the position of the actuators 91, 92.

The power unit 120 can also comprise a rechargeable battery 123 chargeable from the outside by an external power supply/charger unit 112 sending wireless energy.

The adjustment can be controlled by an electronic remote control unit 124 adapted to receive and transmit signals from a transmitter/receiver 106 located outside the body of a treated patient.

The hydraulic device preferably comprises a device positioning system such as a fluid volume or flow measurement or any other sensor input to see the position of the adjustment device. A sensor sensing elongation, for example a capacitance sensor or impedance sensor or any sensor sensing movement or a specific position is preferably provided, here indicated as 125, a sensor communicating with the control unit 124.

Alternatively the schematic FIG. 5 may also instead show a mechanical device 80. In such a case a mechanical wire is outlined as 110 adapted to operate said mechanical device. The power unit 120 may in such a case instead comprise a motor 121 a servo 123 and as before the control unit 124 and sensor 125. The rechargeable power supply may instead be indicated by the unit 122. The motor may of course be placed directly in the mechanical unit 80, wherein the mechanical wire 110 instead is an electrical wire.

The inventions also concern a device for bone adjustment in a mammal, which according to an embodiment comprises two or more anchoring devices for attaching to a bone in said mammal, and an adjustment device for exerting force on said anchoring devices to adjust the distance between or orientation of at least two of said anchoring devices, wherein said anchoring devices and said adjustment device are implanted intramedullary in said mammal and wherein said adjustment device is constructed to postoperatively adjust said distance.

FIG. 6 illustrates an embodiment of the invention, where a device is implanted in a bone (200), said bone having two end portions or epiphysis (201, 202) and a fracture zone (206), said fracture zone also constituting the growth or elongation zone. The medullar cavity (204) is schematically shown in a partial cut-out view and in said cavity, a device (210) is provided, said device having actuators or anchoring means (212, 214) acting on the end portions of the medullar cavity, thus elongating the bone through osteogenesis in the fracture or elongation zone (206).

Figure 7:
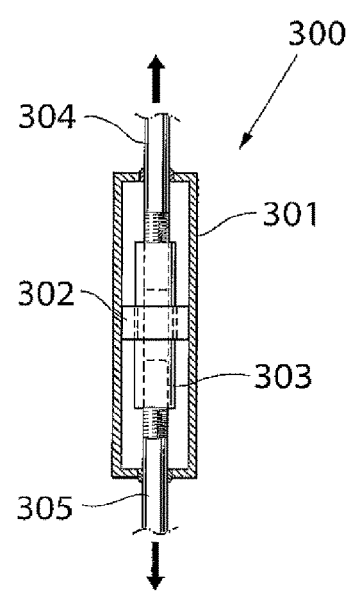
Figure 7:
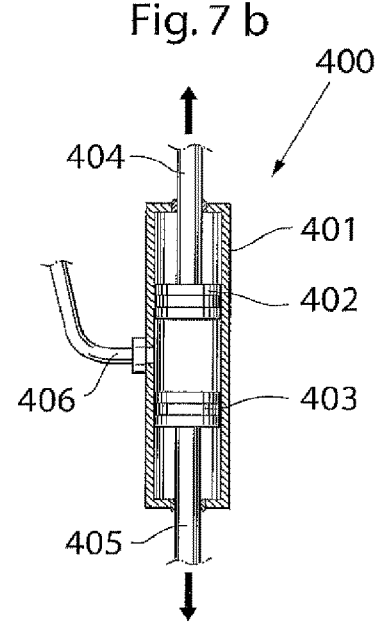

Detailed views of the device 210, according to different embodiments of the invention are shown in FIG. 7.

FIG. 7a schematically shows an embodiment of an extension element or device (300), comprising a housing (301) with an electrical motor (302) acting on a threaded cylinder (303) engaged to two actuators (304, 305). Any mechanical solution may be applied. Preferably the motor uses a servo mechanism to economize force to distance. The control unit, energy source, motor or servo mechanism may all be implanted separately or together in any combination.

FIG. 7b schematically shows another embodiment of an extension element or device (400) comprising a housing (401) with two pistons (402, 403) connected to two actuators (404, 405). The pistons together with the housing and possible additional elements form a hydraulic device, connected via a tubing (406) to a hydraulic power unit (not shown).

In a device according to said embodiment, the adjustment is the lengthening of a bone, the healing of a fracture, the changing of a bone angle, the reshaping of a bone, the compression of a bone, the torsion of a bone or a combination thereof.

A device according to the invention can also be applied to the adjustment of the curvature of the spine. FIG. 8 illustrates an embodiment where a device according to the invention is applied to the adjustment of the curvature of the spine. Detail (a) is a posterior view of the vertebrae of the lower back, vertebrae lumbales, schematically showing two devices (501, 504) according to the invention attached to opposite sides of the spine. For illustration purposes, one device (501) is shown attached to two adjoining vertebrae by two anchoring devices (502, 503) anchored in the corpus vertebrae, whereas another device (504) is shown attached to two non-adjoining vertebrae by two anchoring devices (505, 506). Detail (b) is a lateral detail schematically showing two devices (510, 520) according to the invention attached to opposite sides of the spine by anchoring devices (511, 512, 521, 522). For illustration purposes, one device acts on adjoining vertebrae, whereas the other device acts on non-adjoining vertebrae. This embodiment can be used to adjust the curvature of the spine, to relieve a herniated lumbar disc or the like.

In a device according to any of the embodiments presented herein, said two or more anchoring devices are adapted to engage the bone from the inside of the intramedullar cavity. Preferably said at least two anchoring devices are chosen from a screw, an adhesive, a barb construction, a saw-tooth construction, an expandable element, combinations thereof or other mechanical connecting members. Non-limiting examples of such, anchoring devices are illustrated schematically in FIG. 13a-e, illustrating in turn an arrangement of flanges, a locking device, a screw, a porous end-portion for osseointegration, and a sintered or rugged end-portion with increased friction and/or improved osseointegration properties.

In a device according to any of the embodiments presented herein, the force exerted by the adjustment device is a longitudinal force, extending the length of the bone.

According to an embodiment, said longitudinal force is directed to the end portions of the medullar cavity.

According to another embodiment, the force exerted by the adjustment device is a longitudinal force, adjusting the angle or curvature of the bone. This is illustrated in FIG. 9a schematically showing a frontal view of the right femur (600) exhibiting a curvature deviating from the natural form of this bone. The curvature may be due to a congenital disease or other condition. The dashed lines (601, 602) indicate how the bone can be fractured, preferably by sawing. In one example, wedge shaped parts are removed and the bone divided into sections, here illustrated as three sections. FIG. 9b shows how these three sections of the femur (603) are repositioned to a desired orientation, i.e. a straighter bone. The fracture zones (604, 605) are then used as growth zones in order to compensate for the loss of length due to the removal of bone. Devices (606, 607) according to the invention are then attached via actuators and anchoring devices to said sections, ensuring their position and exerting force to achieve an elongation by distractive osteogenesis. The arrows illustrate schematically that the parts of the bone can be adjusted in relation to each other, for example by adjusting the angle or orientation of said parts.

A related embodiment is illustrated in FIGS. 9c and 9d, where a deformed bone 600 is cut at two locations, 601 and 602, each cut preferably being wedge shaped in order to allow for the straightening of the bone, and devices 610 and 620 according to the inventions inserted into the medullar cavity. Similarly as in FIG. 9b, the arrows illustrate schematically that the parts of the bone can be adjusted in relation to each other, for example by adjusting the angle or orientation of said parts.

According to yet another embodiment, the force exerted by the device applies torque to the bone, adjusting the torsion of the bone along its longitudinal axis. This embodiment is illustrated in FIGS. 9e and 9f, where a bone 600 is cut along the dashed line 630 and optionally along one or more lines, exemplified as 631. One or more implantable device or devices 640 and 650 according to the invention are inserted into the medullar cavity. The arrows indicate that one or several parts of the bone can be adjusted, for example rotated in relation to a joint, or to a section of the bone.

According to another embodiment, freely combinable with any of the embodiments herein, said device is flexible. The advantages of a flexible device are illustrated in FIG. 12a-12d which schematically show a bone 200, having a fracture zone I. An opening II is prepared by ;,a surgeon, allowing the insertion of a device III into the intramedullar cavity IV. FIG. 12b illustrates how the device III is flexible according to an embodiment of the invention, and how this makes it possible to introduce said device into the intramedullar cavity through an opening which is not in straight longitudinal extension to the cavity. Further, FIG. 12c illustrates how the device III, when in place in the cavity IV, retains its original shape and in addition, expands longitudinally to exert a force against the end portions of the cavity. Further, the anchoring devices securely engage the bone. The opening II is preferably closed, e.g. using bone cement. Finally, FIG. 12d illustrates an embodiment where the device III is connected to a power unit V, which can have the components and functions as the power unit 120 shown in FIG. 5.

According to another embodiment, the adjustment device comprises a hydraulic device for said bone adjustment, to control the amount of force exerted by the device onto said anchoring devices. Preferably said hydraulic device comprises a cylinder and piston.

According to another embodiment, the hydraulic device comprises a mechanical multi step locking mechanism, locking the hydraulic device in its new position after adjustment. Said mechanical multi step locking mechanism may comprise at least one of a sprint, a elongated structure using the principle of saw teeth, flanges, barbs or a bonnet band, a nut, a gearbox, or a spring loaded locking principle.

According to another embodiment, the hydraulic device comprises hydraulic fluid and a reservoir containing said fluid, adapted to move said fluid to said adjustment device. Preferably said hydraulic fluid is moved from said reservoir to said adjustment device by using a pre-pressurized reservoir or a pump.

According to another embodiment, the hydraulic device comprises a device positioning system such as a fluid volume or flow measurement or any other sensor input to see the position of the adjustment device.

According to another embodiment, the device comprises a control device. Preferably said control device follows a program of incremental changes, set before the device is implanted. Alternatively, said control device follows a program of incremental changes, communicated to the control device after implantation and/or during the treatment. X-ray or ultrasonic follow up may indicate further treatment, decided by the responsible orthopaedic surgeon.

According to another embodiment, said control device comprises an external control unit and an implantable receiver suitable for wireless communication with said external control unit, having a transmitter located outside the body.

According to another embodiment, said control device controls incremental changes of the adjustment device, communicated to the receiver after implantation and/or during the treatment by using said external control unit.

According to another embodiment, freely combinable with any one of the embodiments presented herein, said hydraulic adjustment device is adapted to being stabilized when the bone adjustment is completed. In this embodiment, the hydraulic adjustment device can be filled with a material which stabilizes the position of the adjustment device and permanents the distance between the anchoring devices.

Preferably said material is chosen from a curable foam, a curable gel, a polymer or polymer mixture which solidifies, crosslinks or otherwise attains and retains a stable volume. Alternatively, the hydraulic fluid used in said device is a material chosen from a curable foam, a curable gel, a polymer or polymer mixture which solidifies, crosslinks or otherwise attains and retains a stable volume when the curing, solidification, crosslinking or other reaction is initiated by the user. According to another embodiment, said material chosen from curable foam, a curable gel, a polymer or polymer mixture which solidifies, crosslinks or otherwise attains and retains a stable volume, is added to the device, partially or completely replacing the hydraulic fluid.

According to another embodiment, the adjustment device comprises a mechanical device for said bone adjustment. Preferably said adjustment device is operated by an operation device, such as motor.

According to another embodiment, the adjustment device comprises a control device, wherein the operation device is controlled by said control device.

According to another embodiment, the motor comprises a motor or device positioning system such as a tachometer or any other sensor input to see the position of the adjustment device.

According to another embodiment, the mechanical device for said bone adjustment comprises at least one nut and screw.

According to another embodiment, the mechanical device for said bone adjustment comprises at least one gearbox.

According to yet another embodiment, the mechanical device for said bone adjustment comprises a servo mechanism or mechanical amplifier.

According to any one of the embodiments herein, the device is adapted for exerting an intermittent and/or oscillating force.

According to any one of the embodiments herein, the device comprises a locking device which allows extension of the device but substantially prevents contraction.

Another embodiment of the inventions is a method for bone adjustment in a mammal, wherein a hydraulic or mechanical device according to any one of the above embodiments is used and implanted in the body of said mammal.

According to another embodiment, the device is implanted intramedullary in the body of said mammal, exerting a force to anchoring devices anchored to the inside of said bone.

According to another embodiment of the method, said bone adjustment is the lengthening of a bone, the healing of a fracture, the changing of a bone angle, he reshaping of a bone, the torsion of a bone or a combination thereof.

According to one embodiment, said adjustment is a step in a treatment to correct a limb discrepancy caused by a congenital condition deformation or previous trauma.

According to another embodiment, said adjustment is reshaping or lengthening of a bone involving distraction osteogenesis treatment.

According to yet another embodiment, said adjustment is the reshaping or lengthening of a bone as a step of correcting a congenital deformation.

According to a further embodiment, said adjustment is the reshaping or lengthening of a bone as a step of a cosmetic treatment.

According to any of the above embodiments of the method, reshaping is one of changing the angle or curvature of a bone, changing the torsion of a bone, changing the angle between the diaphysis and the epiphysis, changing the thickness of a bone or a combination thereof.

Another embodiment of the inventions is a method for bone adjustment in a mammal wherein a device is implanted intramedullary in the body of said mammal, wherein said device is a hydraulic device exerting a force to anchoring devices anchored in said bone and a control device which controls the amount of force exerted by the device.

Another embodiment of the inventions is a method for bone adjustment in a mammal wherein a device is implanted intramedullary in the body of said mammal, wherein said device is a mechanical device exerting a force to anchoring devices anchored in said bone and a control device which controls the amount of force exerted by the device.

In any of the above methods, said control device follows a program of incremental changes, set before the device is implanted. Alternatively, said control device follows a program of incremental changes, communicated to the control device after implantation and/or during the treatment.

According to any of the embodiments of the method, said device is stabilized when the treatment is completed. Preferably said device is stabilized by filling the device with a material which stabilizes the position of the adjustment device and permanents the distance between the anchoring devices. In this method said material is chosen from curable foam, a curable gel, a polymer or polymer mixture which solidifies, crosslinks or otherwise attains and retains a stable volume.

Alternatively, the device is a hydraulic device and the hydraulic fluid is a material chosen from a curable foam, a curable gel, a polymer or polymer mixture which solidifies, crosslinks or otherwise attains and retains a stable volume when the curing, solidification crosslinking or other reaction is initiated by the user.

According to another embodiment, the device is a hydraulic device and a material chosen from curable foam, a curable gel, a polymer or polymer mixture which solidifies, crosslinks or otherwise attains and retains a stable volume, is added to said device, partially or completely replacing the hydraulic fluid.

Another embodiment of the inventions is a method for distractive osteogenesis where the fractured bone is subjected to an intermittent and/or oscillating force using an implanted hydraulic or mechanical device.

Another embodiment of the inventions is a method for treating a bone dysfunction of a mammal patient by providing a device for bone adjustment comprising at least two anchoring devices according to any one of embodiments of a device according to the inventions, the method comprising the steps of
  i. inserting a needle or tube-like instrument into a cavity of said mammal patient;
  ii. inflating said cavity by introducing a fluid through said needle or tube-like instrument and thereby expanding said cavity;
  iii. placing at least two laparoscopic trocars in said cavity;
  iv. inserting a camera through one of said laparoscopic trocars into said cavity;
  v. inserting at least one dissecting tool through one of said at least two laparoscopic trocars;
  vi. dissecting an area of the dysfunctional bone;
  vii. placing the device for bone adjustment, and anchoring devices in the medullar cavity of said bone;
  viii. anchoring said anchoring devices in contact with said bone;
  ix. closing the mammal body preferably in layers; and
  x. non-invasively adjusting said bone postoperatively.

Another embodiment of the inventions is a method of treating a bone dysfunction of a mammal patient by providing a device for bone adjustment comprising at least two anchoring devices according to any one the embodiments of the device according to the inventions, comprising the steps of:
  i. cutting the skin of said human patient;
  ii. dissecting an area of the dysfunctional bone;
  iii. placing the device in the medullar cavity of said bone;
  iv. anchoring said anchoring devices in contact with said bone;
  v. closing the mammal body preferably in layers; and
  vi. non-invasively adjusting said bone postoperatively.

According to a further embodiment, the method of treating a mammal patient further comprises the step of withdrawing the instruments.

According to a further embodiment, the method of treating a mammal patient further comprises the step of closing the skin using sutures or staples.

According to a further embodiment, the step of dissecting includes dissecting an area of the arm or leg comprising, dissecting an area of at least one of the following bones; clavicula, scapula, humerus, radius, ulna, pelvic bone, femur, tibia, fibula or calcaneus.

According to a further embodiment, the step of dissecting includes dissecting an area of the arm or leg comprising, dissecting an area of at least one of the following joints; shoulder, elbow, hip, knee, hand and foot.

According to a further embodiment of the method, an opening into the medullar cavity is made by drilling.

Another embodiment of the inventions relates to a system comprising an apparatus or device according to any one of the embodiments presented herein.

According to a further embodiment, said system further comprises at least one switch implantable in the patient for manually and non-invasively controlling the apparatus.

According to a further embodiment, said system further comprises a hydraulic device having an implantable hydraulic reservoir, which is hydraulically connected to the apparatus, wherein the apparatus is adapted to be non-invasively regulated by manually pressing the hydraulic reservoir.

According to a further embodiment, said system further comprises a wireless remote control for non-invasively controlling the apparatus.

According to an embodiment, said wireless remote control comprises at least one external signal transmitter and/or receiver, further comprising an internal signal receiver and/or transmitter implantable in the patient for receiving signals transmitted by the external signal transmitter or transmitting signals to the external signal receiver.

According to an embodiment, said wireless remote control transmits at least one wireless control signal for controlling the apparatus.

According to an embodiment, said wireless control signal comprises a frequency, amplitude, or phase modulated signal or a combination thereof.

According to an embodiment, said wireless remote control transmits an electromagnetic carrier wave signal for carrying the control signal.

According to yet another embodiment, said system further comprises a wireless energy-transmission device for non-invasively energizing implantable energy consuming components of the apparatus with wireless energy.

Wireless transmission of energy gives additional advantages to the inventive method and device. These embodiments will be disclosed in the following with reference to the schematic illustrations attached.

FIG. 11 illustrates a system for treating a disease comprising an apparatus 301 according to an embodiment of the present invention placed in the lower leg of a patient. An implanted energy-transforming device 302 is adapted to supply energy consuming components of the apparatus with energy via a power supply line 303. An external energy-transmission device 304 for non-invasively energizing the apparatus 301 transmits energy by at least one wireless energy signal. The implanted energy-transforming device 302 transforms energy from the wireless energy signal into electric energy which is supplied via the power supply line 303. Another external device 305 is illustrated, schematically showing a device capable of transmitting control signals to the apparatus 301, and optionally receiving signals transmitted by the apparatus 301, for example information about the position, energy level, tension, pressure, temperature or other relevant information registered by one or more sensors (not shown) included in the apparatus.

The wireless energy signal may include a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal may include an electric or magnetic field, or a combined electric and magnetic field.

The wireless energy-transmission device 304 may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Generally speaking, the energy-transforming device 302 is provided for transforming wireless energy of a first form transmitted by the energy-transmission device 304 into energy of a second form, which typically is different from the energy of the first form. The implanted apparatus 301 is operable in response to the energy of the second form. The energy-transforming device 302 may directly power the apparatus with the second form energy, as the energy-transforming device 302 transforms the first form energy transmitted by the energy-transmission device 304 into the second form energy. The system may further include an implantable accumulator, wherein the second form energy is used at least partly to charge the accumulator.

Alternatively, the wireless energy transmitted by the energy-transmission device 304 may be used to directly power the apparatus, as the wireless energy is being transmitted by the energy-transmission device 304 Where the system comprises an operation device for operating the apparatus, as will be described below, the wireless energy transmitted by the energy-transmission device 304 may be used to directly power the operation device to create kinetic energy for the operation of the apparatus.

The wireless energy of the first form may comprise sound waves and the energy-transforming device 302 may include a piezo-electric element for transforming the sound waves into electric energy. The energy of the second form may comprise electric energy in the form of a direct current or pulsating direct current, or a combination of a direct current and pulsating direct current, or an alternating current or a combination of a direct and alternating current. Normally, the apparatus comprises electric components that are energized with electrical energy. Other implantable electric components of the system may be at least one voltage level guard or at least one constant current guard connected with the electric components of the apparatus.

Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transmission device may be controlled from outside the patient's body to release electromagnetic wireless energy, and the released electromagnetic wireless energy is used for operating the apparatus. Alternatively, the energy-transmission device is controlled from outside the patient's body to release non-magnetic wireless energy, and the released non-magnetic wireless energy is used for operating the apparatus.

The external energy-transmission device 304 also includes a wireless remote control having an external signal transmitter for transmitting a wireless control signal for non-invasively controlling the apparatus. The control signal is received by an implanted signal receiver which may be incorporated in the implanted energy-transforming device 302 or be separate there from.

The wireless control signal may include a frequency, amplitude, or phase modulated signal or a combination thereof. Alternatively, the wireless control signal includes an analogue or a digital signal, or a combination of an analogue and digital signal. Alternatively, the wireless control signal comprises an electric or magnetic field, or a combined electric and magnetic field.

The wireless remote control may transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control preferably transmits an electromagnetic carrier wave signal for carrying the digital or analogue control signals.

Figure 1:
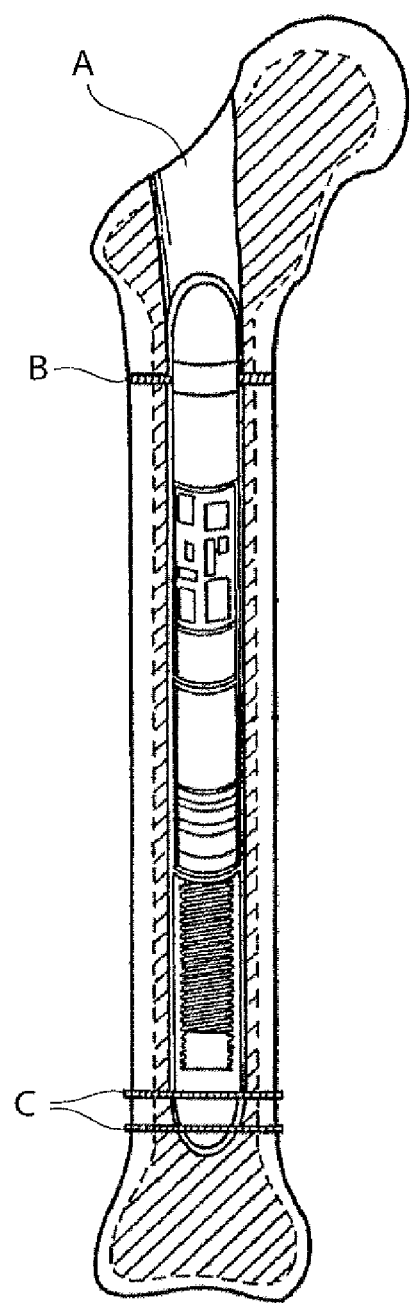
Figure 2:
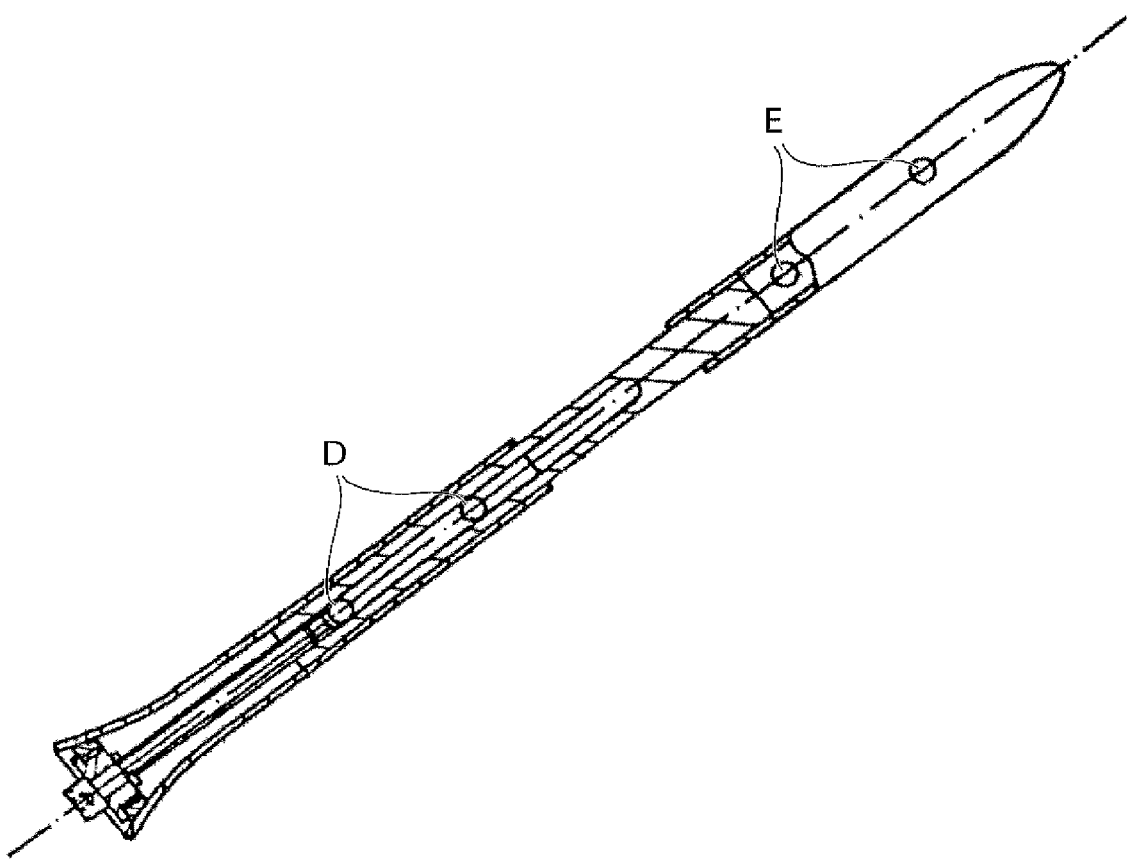
Figure 3:
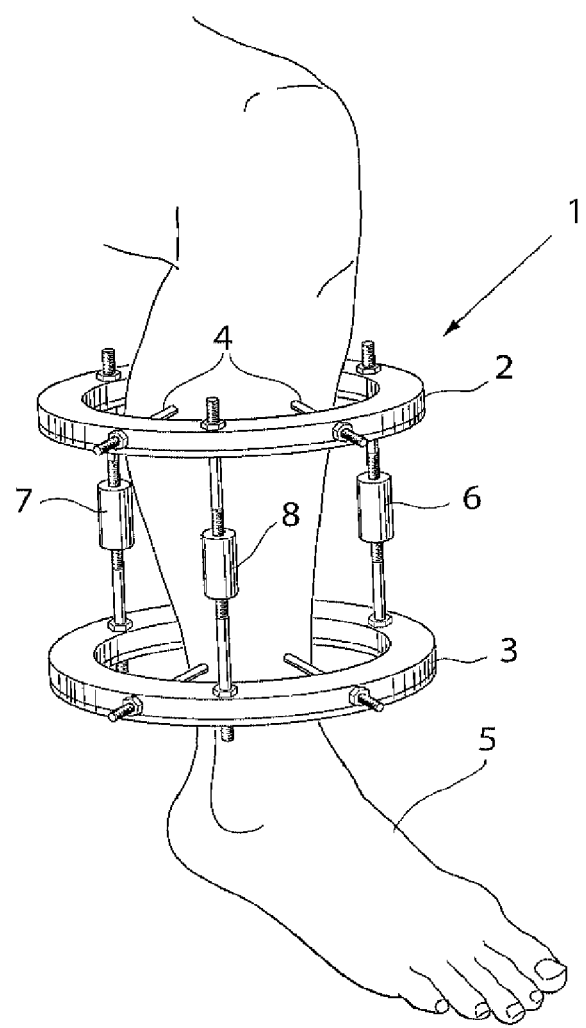

FIG. 14 illustrates the system of FIG. 1 in the form of a more generalized block diagram showing the apparatus 301, the energy-transforming device 302 powering the apparatus 301 via power supply line 303, and the external energy-transmission device 304, The patient's skin 305, generally shown by a vertical line, separates the interior of the patient to the right of the line from the exterior to the left of the line.

Figure 10:
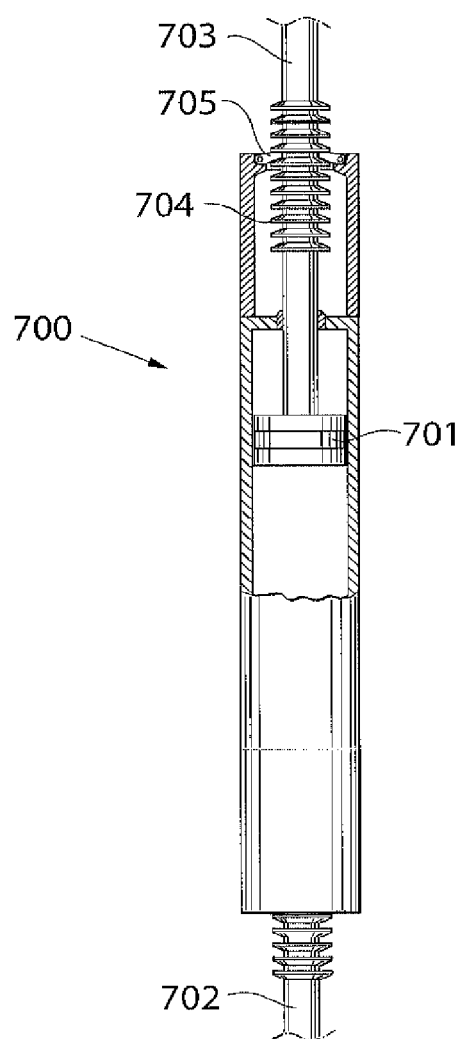
Figure 10:
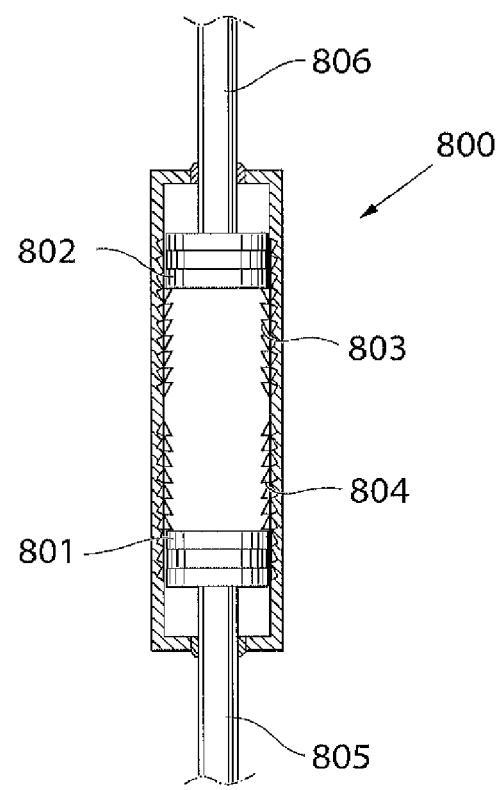

FIG. 15 shows an embodiment of the invention identical to that of FIG. 10, except that a reversing device in the form of an electric switch 306 operable for example by polarized energy also is implanted in the patient for reversing the apparatus 301. When the switch is operated by polarized energy the wireless remote control of the external energy-transmission device 304 transmits a wireless signal that carries polarized energy and the implanted energy-transforming device 302 transforms the wireless polarized energy into a polarized current for operating the electric switch 306. When the polarity of the current is shifted by the implanted energy-transforming device 302 the electric switch 306 reverses the function performed by the apparatus 301.

FIG. 16 shows an embodiment of the invention identical to that of FIG. 14, except that an operation device 307 implanted in the patient for operating the apparatus 301 is provided between the implanted energy-transforming device 302 and the apparatus 301. This operation device can be in the form of a motor 307, such as an electric servomotor. The motor 307 is powered with energy from the implanted energy-transforming device 302, as the remote control of the external energy-transmission device 304 transmits a wireless signal to the receiver of the implanted energy-transforming device 302.

FIG. 17 shows an embodiment of the invention identical to that of FIG. 14, except that it also comprises an operation device is in the form of an assembly 308 including a motor/pump unit 309 and a fluid reservoir 310 is implanted in the patient. In this case the apparatus 301 is hydraulically operated, i.e. hydraulic fluid is pumped by the motor/pump unit 309 from the fluid reservoir 310 through a conduit 311 to the apparatus 301 to operate the apparatus, and hydraulic fluid is pumped by the motor/pump unit 309 back from the apparatus 301 to the fluid reservoir 310 to return the apparatus to a starting position. The implanted energy-transforming device 302 transforms wireless energy into a current, for example a polarized current, for powering the motor/pump unit 309 via an electric power supply line 312.

Instead of a hydraulically operated apparatus 301, it is also envisaged that the operation device comprises a pneumatic operation device. In this case, the hydraulic fluid can be pressurized air to be used for regulation and the fluid reservoir is replaced by an air chamber.

In all of these embodiments the energy-transforming device 302 may include a rechargeable accumulator like a battery or a capacitor to be charged by the wireless energy and supplies energy for any energy consuming part of the system.

As an alternative, the wireless remote control described above may be replaced by manual control of any implanted part to make contact with by the patient's hand most likely indirect, for example a press button placed under the skin.

Figure 18:
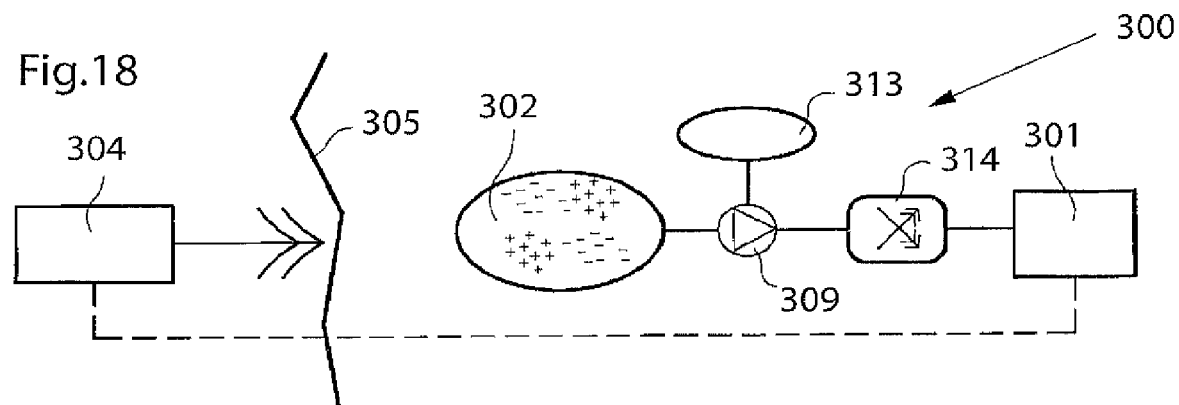

FIG. 18 shows an embodiment of the invention comprising the external energy-transmission device 304 with its wireless remote control, the apparatus 301, in this case hydraulically operated, and the implanted energy-transforming device 302, and further comprising a hydraulic fluid reservoir 313, a motor/pump unit 309 and an reversing device in the form of a hydraulic valve shifting device 314, all implanted in the patient. Of course the hydraulic operation could easily be performed by just changing the pumping direction and the hydraulic valve may therefore be omitted. The remote control may be a device separated from the external energy-transmission device or included in the same. The motor of the motor/pump unit 309 is an electric motor. In response to a control signal from the wireless remote control of the external energy-transmission device 304, the implanted energy-transforming device 302 powers the motor/pump unit 309 with energy from the energy carried by the control signal, whereby the motor/pump unit 309 distributes hydraulic fluid between the hydraulic fluid reservoir 313 and the apparatus 301. The remote control of the external energy-transmission device 304 controls the hydraulic valve shifting device 314 to shift the hydraulic fluid flow direction between one direction in which the fluid is pumped by the motor/pump unit 309 from the hydraulic fluid reservoir 313 to the apparatus 301 to operate the apparatus, and another opposite direction in which the fluid is pumped by the motor/pump unit 309 back from the apparatus 301 to the hydraulic fluid reservoir 313 to return the apparatus to a starting position.

Figure 19:
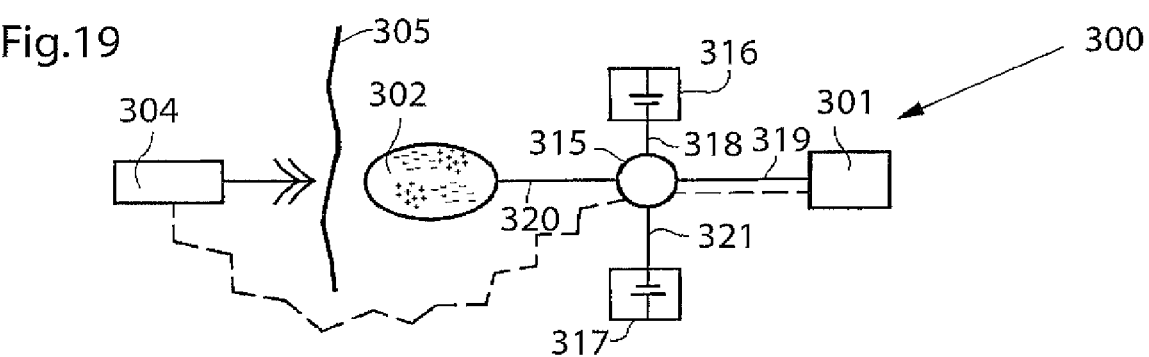

FIG. 19 shows an embodiment of the invention comprising the external energy-transmission device 304 with its wireless remote control, the apparatus 301, the implanted energy-transforming device 302, an implanted internal control unit 315 controlled by the wireless remote control of the external energy-transmission device 304, an implanted accumulator 316 and an implanted capacitor 317. The internal control unit 315 arranges storage of electric energy received from the implanted energy-transforming device 302 in the accumulator 316, which supplies energy to the apparatus 301. In response to a control signal from the wireless remote control of the external energy-transmission device 304, the internal control unit 315 either releases electric energy from the accumulator 316 and transfers the released energy via power lines 318 and 319, or directly transfers electric energy from the implanted energy-transforming device 302 via a power line 320, the capacitor 317, which stabilizes the electric current, a power line 321 and the power line 319, for the operation of the apparatus 301.

The internal control unit is preferably programmable from outside the patient's body. In a preferred embodiment, the internal control unit is programmed to regulate the apparatus 301 according to a pre-programmed time-schedule or to input from any sensor sensing any possible physical parameter of the patient or any functional parameter of the system.

In accordance with an alternative, the capacitor 317 in the embodiment of FIG. 19 may be omitted. In accordance with another alternative, the accumulator 316 in this embodiment may be omitted.

Figure 20:
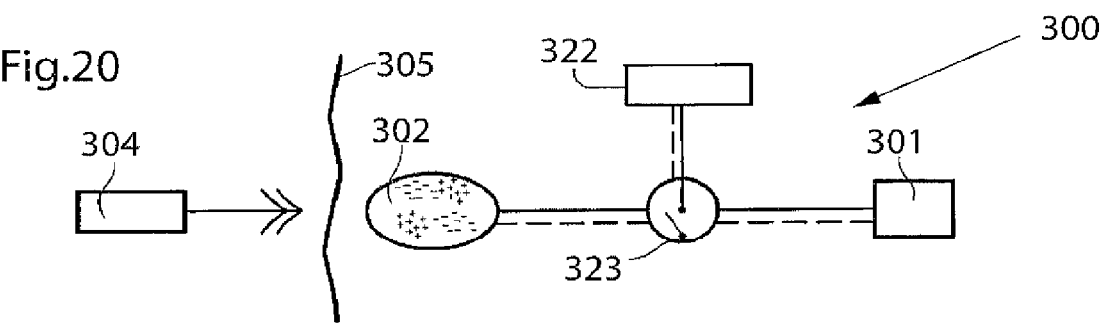

FIG. 20 shows an embodiment of the invention identical to that of FIG. 14, except that a battery 322 for supplying energy for the operation of the apparatus 301 and an electric switch 323 for switching the operation of the apparatus 301 also are implanted in the patient. The electric switch 323 may be controlled by the remote control and may also be operated by the energy supplied by the implanted energy-transforming device 302 to switch from an off mode, in which the battery 322 is not in use, to an on mode, in which the battery 322 supplies energy for the operation of the apparatus 301.

Figure 21:
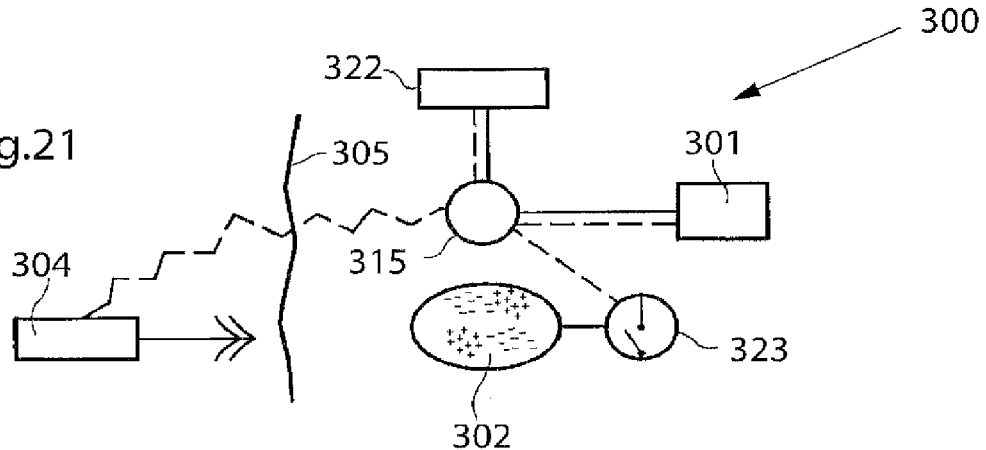

FIG. 21 shows an embodiment of the invention identical to that of FIG. 20, except that an internal control unit 315 controllable by the wireless remote control of the external energy-transmission device 304 also is implanted in the patient. In this case, the electric switch 323 is operated by the energy supplied by the implanted energy-transforming device 302 to switch from an off mode, in which the wireless remote control is prevented from controlling the internal control unit 315 and the battery is not in use, to a standby mode, in which the remote control is permitted to control the internal control unit 315 to release electric energy from the battery 322 for the operation of the apparatus 301.

Figure 22:
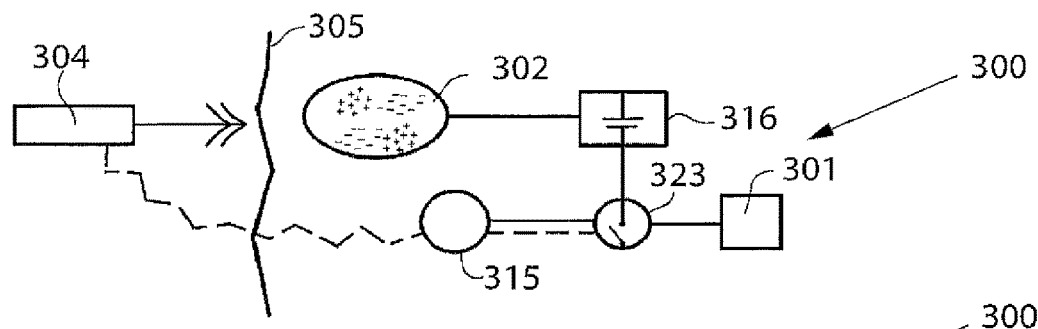

FIG. 22 shows an embodiment of the invention identical to that of FIG. 21, except that an accumulator 316 is substituted for the battery 322 and the implanted components are interconnected differently. In this case, the accumulator 316 stores energy from the implanted energy-transforming device 302. In response to a control signal from the wireless remote control of the external energy-transmission device 304, the internal control unit 315 controls the electric switch 323 to switch from an off mode, in which the accumulator 316 is not in use, to an on mode, in which the accumulator 316 supplies energy for the operation of the apparatus 301. The accumulator may be combined with or replaced by a capacitor.

Figure 23:
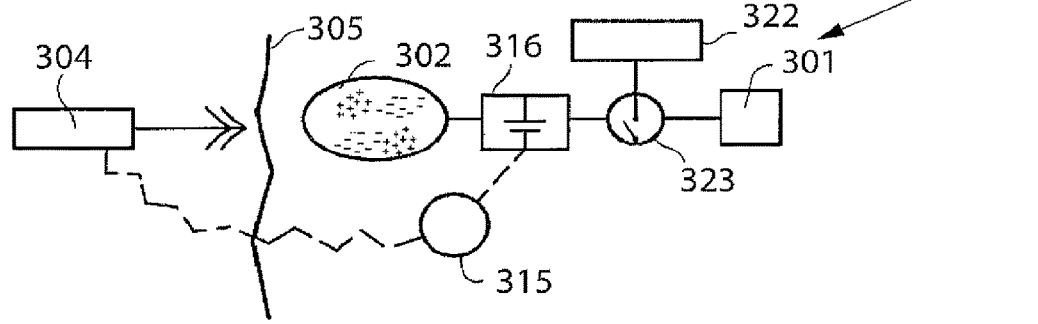

FIG. 23 shows an embodiment of the invention identical to that of FIG. 22, except that a battery 322 also is implanted in the patient and the implanted components are interconnected differently. In response to a control signal from the wireless remote control of the external energy-transmission device 304, the internal control unit 315 controls the accumulator 316 to deliver energy for operating the electric switch 323 to switch from an off mode, in which the battery 322 is not in use, to an on mode, in which the battery 322 supplies electric energy for the operation of the apparatus 301.

Alternatively, the electric switch 323 may be operated by energy supplied by the accumulator 316 to switch from an off mode, in which the wireless remote control is prevented from controlling the battery 322 to supply electric energy and is not in use, to a standby mode, in which the wireless remote control is permitted to control the battery 322 to supply electric energy for the operation of the apparatus 301.

It should be understood that the switch 323 and all other switches in this application should be interpreted in its broadest embodiment. This means a transistor, MCU, MCPU, ASIC, FPGA or a DA converter or any other electronic component or circuit that may switch the power on and off. Preferably the switch is controlled from outside the body, or alternatively by an implanted internal control unit.

Figure 24:
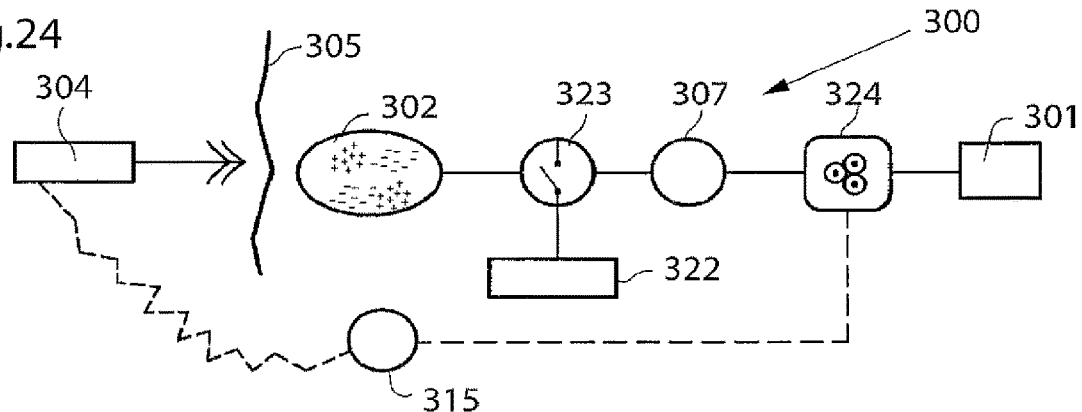

FIG. 24 shows an embodiment of the invention identical to that of FIG. 20, except that a motor 307, a mechanical reversing device in the form of a gear box 324, and an internal control unit 315 for controlling the gear box 324 also are implanted in the patient. The internal control unit 315 controls the gear box 324 to reverse the function performed by the apparatus 301 (mechanically operated). Even simpler is to switch the direction of the motor electronically. The gear box interpreted in its broadest embodiment may stand for a servo arrangement saving force for the operation device in favour of longer stroke to act.

This is also illustrated in FIG. 39 which schematically shows a device according to an embodiment of the invention where an implantable device 2000 comprises a motor 2010 operationally connected to a gear box 2020 and an adjustment device 2030, where the speed and/or effect of the motor 2010 is controlled by a control unit 2040. According to one embodiment, said control unit 2040 both senses the speed of the motor 2010 and adjusts the same, and optionally also senses the output speed of the gear box 2020, driving the adjustment device 2030. According to another embodiment, said control unit 2040 comprises a feed-back loop, sensing the speed o the motor, and adjusting the same to a desired value. In another embodiment, no gear box is present, and the control unit 2040 both senses the speed of the motor and adjusts the same.

Figure 25:
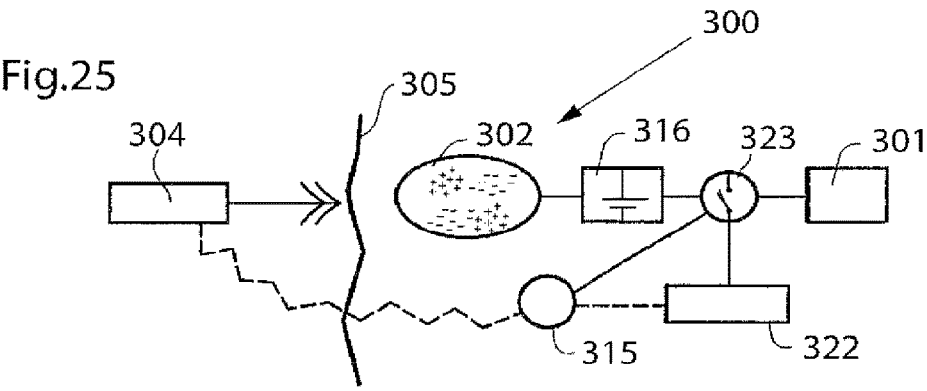

FIG. 25 shows an embodiment of the invention identical to that of FIG. 23 except that the implanted components are interconnected differently. Thus, in this case the internal control unit 315 is powered by the battery 322 when the accumulator 316, suitably a capacitor, activates the electric switch 323 to switch to an on mode. When the electric switch 323 is in its on mode the internal control unit 315 is permitted to control the battery 322 to supply, or not supply, energy for the operation of the apparatus 301.

Figure 26:
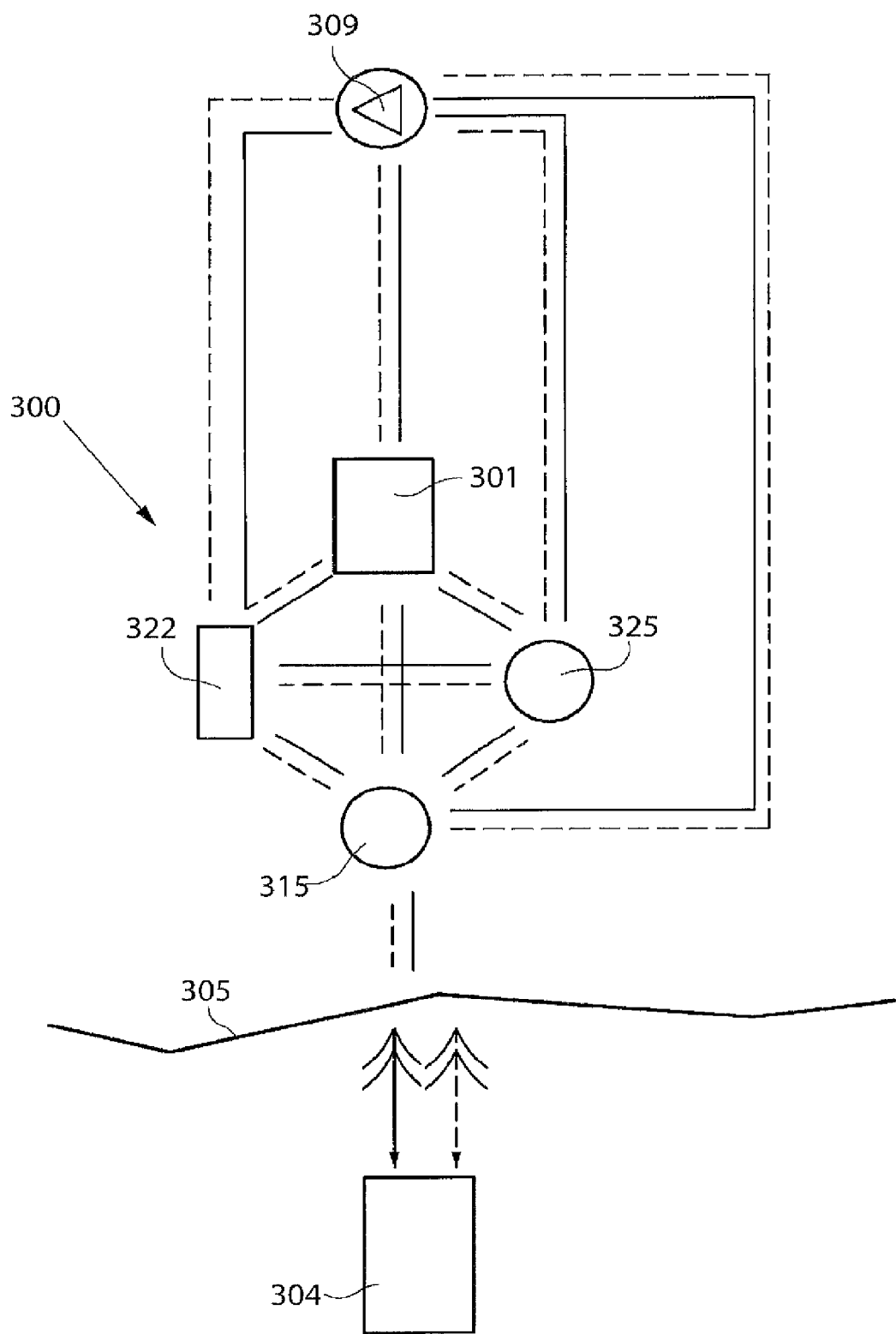

FIG. 26 schematically shows conceivable combinations of implanted components of the apparatus for achieving various communication options. Basically, there are the apparatus 301, the internal control unit 315, motor or pump unit 309, and the external energy-transmission device 304 including the external wireless remote control. As already described above the wireless remote control transmits a control signal which is received by the internal control unit 315, which in turn controls the various implanted components of the apparatus.

A feedback device, preferably comprising a sensor or measuring device 325, may be implanted in the patient for sensing a physical parameter of the patient, The physical parameter may be at least one selected from the group consisting of pressure, volume, diameter, stretching, elongation, extension, movement, bending, elasticity, muscle contraction, nerve impulse, body temperature, blood pressure, blood flow, heartbeats and breathing. The sensor may sense any of the above physical parameters. For example, the sensor may be a pressure or motility sensor. Alternatively, the sensor 325 may be arranged to sense a functional parameter. The functional parameter may be correlated to the transfer of energy for charging an implanted energy source and may further include at least one selected from the group of parameters consisting of; electricity, pressure, volume, diameter, stretch, elongation, extension, movement, bending, elasticity, temperature and flow.

The feedback may be sent to the internal control unit or out to an external control unit preferably via the internal control unit. Feedback may be sent out from the body via the energy transfer system or a separate communication system with receiver and transmitters.

The internal control unit 315, or alternatively the external wireless remote control of the external energy-transmission device 304, may control the apparatus 301 in response to signals from the sensor 325. A transceiver may be combined with the sensor 325 for sending information on the sensed physical parameter to the external wireless remote control. The wireless remote control may comprise a signal transmitter or transceiver and the internal control unit 315 may comprise a signal receiver or transceiver. Alternatively, the wireless remote control may comprise a signal receiver or transceiver and the internal control unit 315 may comprise a signal transmitter or transceiver. The above transceivers, transmitters and receivers may be used for sending information or data related to the apparatus 301 from inside the patients body to the outside thereof.

Where the motor/pump unit 309 and battery 322 for powering the motor/pump unit 309 are implanted, information related to the charging of the battery 322 may be fed back. To be more precise, when charging a battery or accumulator with energy feedback information related to said charging process is sent and the energy supply is changed accordingly.

FIG. 27 shows an alternative embodiment wherein the apparatus 301 is regulated from outside the patient's body. The system 300 comprises a battery 322 connected to the apparatus 301 via a subcutaneous electric switch 326. Thus, the regulation of the apparatus 301 is performed non-invasively by manually pressing the subcutaneous switch, whereby the operation of the apparatus 301 is switched on and off. It will be appreciated that the shown embodiment is a simplification and that additional components, such as an internal control unit or any other part disclosed in the present application can be added to the system. Two subcutaneous switches may also be used. In the preferred embodiment one implanted switch sends information to the internal control unit to perform a certain predetermined performance and when the patient press the switch again the performance is reversed.

Figure 28:
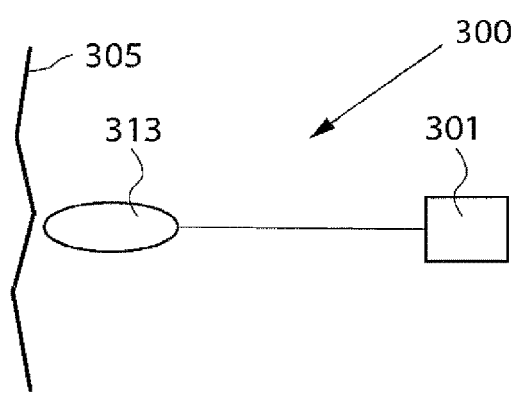

FIG. 28 shows an alternative embodiment, wherein the system 300 comprises a hydraulic fluid reservoir 313 hydraulically connected to the apparatus. Non-invasive regulation is performed by manually pressing the hydraulic reservoir connected to the apparatus.

The system may include an external data communicator and an implantable internal data communicator communicating with the external data communicator. The internal communicator feeds data related to the apparatus or the patient to the external data communicator and/or the external data communicator feeds data to the internal data communicator.

FIG. 29 schematically illustrates an arrangement of the system that is capable of sending information from inside the patient's body to the outside thereof to give feedback information related to at least one functional parameter of the apparatus or system, or related to a physical parameter of the patient, in order to supply an accurate amount of energy to an implanted internal energy receiver 302 connected to implanted energy consuming components of the apparatus 301. Such an energy receiver 302 may include an energy source and/or an energy-transforming device. Briefly described, wireless energy is transmitted from an external energy source 304a located outside the patient and is received by the internal energy receiver 302 located inside the patient. The internal energy receiver is adapted to directly or indirectly supply received energy to the energy consuming components of the apparatus 301. An energy balance is determined between the energy received by the internal energy receiver 302 and the energy used for the apparatus 301, and the transmission of wireless energy is then controlled based on the determined energy balance. The energy balance thus provides an accurate indication of the correct amount of energy needed, which is sufficient to operate the apparatus 301 properly, but without causing undue temperature rise.

In FIG. 29 the patient's skin is indicated by a vertical line 305. Here, the energy receiver comprises an energy-transforming device 302 located inside the patient, preferably just beneath the patient's skin 305. Generally speaking, the implanted energy-transforming device 302 may be placed in the abdomen, thorax, muscle fascia (e.g. in the abdominal wall), subcutaneously, or at any other suitable location. The implanted energy-transforming device 302 is adapted to receive wireless energy E transmitted from the external energy-source 304*a* provided in an external energy-transmission device 304 located outside the patient's skin 305 in the vicinity of the implanted energy-transforming device 302

As is well known in the art, the wireless energy E may generally be transferred by means of any suitable Transcutaneous Energy Transfer (TET) device, such as a device including a primary coil arranged in the external energy source 304*a* and an adjacent secondary coil arranged in the implanted energy-transforming device 302. When an electric current is fed through the primary coil, energy in the form of a voltage is induced in the secondary coil which can be used to power the implanted energy consuming components of the apparatus, e.g. after storing the incoming energy in an implanted energy source, such as a rechargeable battery or a capacitor. However, the present invention is generally not limited to any particular energy transfer technique, TET devices or energy sources, and any kind of wireless energy may be used.

The amount of energy received by the implanted energy receiver may be compared with the energy used by the implanted components of the apparatus. The term "energy used" is then understood to include also energy stored by implanted components of the apparatus. A control device includes an external control unit 304*b* that controls the external energy source 304*a* based on, the determined energy balance to regulate the amount of transferred energy. In order to transfer the correct amount of energy, the energy balance and the required amount of energy is determined by means of a determination device including an implanted internal control unit 315 connected to the apparatus 301. The internal control unit 315 may thus be arranged to receive various measurements obtained by suitable sensors or the like, not shown, measuring certain characteristics of the apparatus 301, somehow reflecting the required amount of energy needed for proper operation of the apparatus 301 Moreover, the current condition of the patient may also be detected by means of suitable measuring devices or sensors, in order to provide parameters reflecting the patient's condition. Hence, such characteristics and/or parameters may be related to the current state of the apparatus 301, such as power consumption, operational mode and temperature, as well as the patients condition reflected by parameters such as; body temperature, blood pressure, heartbeats and breathing. Other kinds of physical parameters of the patient and functional parameters of the device are described elsewhere.

Furthermore, an energy source in the form of an accumulator 316 may optionally be connected to the implanted energy-transforming device 302 for accumulating received energy for later use by the apparatus 301. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the apparatus 301, and also to avoid excessive heating, it is clearly understood that the battery should be charged optimally by receiving a correct amount of energy from the implanted energy-transforming device 302, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 315. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 315 of the determination device is adapted to determine the energy balance and/or the currently required amount of energy, (either energy per time unit or accumulated energy) based on measurements made by the above-mentioned sensors or measuring devices of the apparatus 301, or the patient, or an implanted energy source if used, or any combination thereof. The internal control unit 315 is further connected to an internal signal transmitter 327, arranged to transmit a control signal reflecting the determined required amount of energy, to an external signal receiver 304*c* connected to the external control unit 304*b*. The amount of energy transmitted from the external energy source 304*a* may then be regulated in response to the received control signal.

Alternatively, the determination device may include the external control unit 304*b*. In this alternative, sensor measurements can be transmitted directly to the external control unit 304*b* wherein the energy balance and/or the currently required amount of energy can be determined by the external control unit 304*b*, thus integrating the above-described function of the internal control unit 315 in the external control unit 304*b*. In that case, the internal control unit 315 can be omitted and the sensor measurements are supplied directly to the internal signal transmitter 327 which sends the measurements over to the external signal receiver 304*c* and the external control unit 304*b*. The energy balance and the currently required amount of energy can then be determined by the external control unit 304*b* based on those sensor measurements.

Hence, the present solution according to the arrangement of FIG. 25 employs the feedback of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming components of the apparatus. The apparatus may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the apparatus.

The internal signal transmitter 327 and the external signal receiver 304*c* may be implemented as separate units using suitable signal transfer means, such as radio, IR (Infrared) or ultrasonic signals. Alternatively, the internal signal transmitter 327 and the external signal receiver 304*c* may be integrated in the implanted energy-transforming device 302 and the external energy source 304*a*, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy system. In accordance with the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this system in the arrangement of FIG. 29, the switch 326 is either separate and controlled by the internal control unit 315, or integrated in the internal control unit 315. It should be understood that the switch 326 should be interpreted in its broadest embodiment. This means a transistor, MCU, MCPU, ASIC FPGA or a DA converter or any other electronic component or circuit that may switch the power on and off.

To conclude, the energy supply arrangement illustrated in FIG. 29 may operate basically in the following manner. The energy balance is first determined by the internal control unit 315 of the determination device. A control signal reflecting the required amount of energy is also created by the internal control unit 315, and the control signal is transmitted from the internal signal transmitter 327 to the external signal receiver 304c. Alternatively, the energy balance can be determined by the external control unit 304b instead depending on the implementation, as mentioned above. In that case, the control signal may carry measurement results from various sensors. The amount of energy emitted from the external energy source 304a can then be regulated by the external control unit 304b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 304a, such as voltage, current, amplitude, wave frequency and pulse characteristics.

This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factors information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factors between the first and second coils. The transmitted energy may be regulated depending on the obtained coupling factor.

With reference to FIG. 30, although wireless transfer of energy for operating the apparatus has been described above to enable non-invasive operation, it will be appreciated that the apparatus can be operated with wire bound energy as well.

Such an example is shown in FIG. 30, wherein an external switch 326 is interconnected between the external energy source 304a and an operation device, such as an electric motor 307 operating the apparatus 301. An external control unit 304b controls the operation of the external switch 326 to effect proper operation of the apparatus 301.

FIG. 31 illustrates different embodiments for how received energy can be supplied to and used by the apparatus 301. Similar to the example of FIG. 29, an internal energy receiver 302 receives wireless energy E from an external energy source 304a which is controlled by a transmission control unit 304b. The internal energy receiver 302 may comprise a constant voltage circuit, indicated as a dashed box "constant V" in the figure, for supplying energy at constant voltage to the apparatus 301. The internal energy receiver 302 may further comprise a constant current circuit, indicated as a dashed box "constant C" in the figure, for supplying energy at constant current to the apparatus 301.

The apparatus 301 comprises an energy consuming part 301a, which may be a motor, pump, restriction device, or any other medical appliance that requires energy for its electrical operation. The apparatus 301 may further comprise an energy storage device 301b for storing energy supplied from the internal energy receiver 302. Thus, the supplied energy may be directly consumed by the energy consuming part 301a, or stored by the energy storage device 301b, or the supplied energy may be partly consumed and partly stored. The apparatus 301 may further comprise an energy stabilizing unit 301c for stabilizing the energy supplied from the internal energy receiver 302. Thus, the energy may be supplied in a fluctuating manner such that it may be necessary to stabilize the energy before consumed or stored.

The energy supplied from the internal energy receiver 302 may further be accumulated and/or stabilized by a separate energy stabilizing unit 328 located outside the apparatus 301, before being consumed and/or stored by the apparatus 301. Alternatively, the energy stabilizing unit 328 may be integrated in the internal energy receiver 302. In either case, the energy stabilizing unit 328 may comprise a constant voltage circuit and/or a constant current circuit.

It should be noted that FIG. 29 and FIG. 31 illustrate some possible but non-limiting implementation options regarding how the various shown functional components and elements can be arranged and connected to each other. However, the skilled person will readily appreciate that many variations and modifications can be made within the scope of the present invention.

FIG. 32 schematically shows an energy balance measuring circuit of one of the proposed designs of the system for controlling transmission of wireless energy, or energy balance control system. The circuit has an output signal centered on 2.5V and proportionally related to the energy imbalance. The derivative of this signal shows if the value goes up and down and how fast such change takes place. If the amount of received energy is lower than the energy used by the implant, more energy is transferred and thus charged into the energy source. The output signal from the circuit is typically feed to an A/D converter and, converted into a digital format. The digital information can then be sent to the external energy-transmission device allowing it to adjust the level of the transmitted energy. Another possibility is to have a completely analog system that uses comparators comparing the energy balance level with certain maximum and minimum thresholds sending information to external energy-transmission device if the balance drifts out of the max/min window.

The schematic FIG. 32 shows a circuit implementation for a system that transfers energy to the implanted energy components of the apparatus of the present invention from outside of the patient's body using inductive energy transfer. An inductive energy transfer system typically uses an external transmitting coil and an internal receiving coil. The receiving coil, L1, is included in the schematic figure; the transmitting parts of the system are excluded.

The implementation of the general concept of energy balance and the way the information is transmitted to the external energy transmitter can of course be implemented in numerous different ways. The schematic FIG. 28 and the above described method of evaluating and transmitting the information should only be regarded as examples of how to implement the control system.

Circuit Details

In FIG. 32 the symbols Y1, Y2, Y3 and so on symbolize test points within the circuit. The components in the diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

Those skilled in the art will realize that the above various embodiments of the system could be combined in many different ways. For example, the electric switch 306 of FIG. 11 could be incorporated in any of the embodiments of FIGS. 14-20, the hydraulic valve shifting device 314 could be incorporated in another embodiment of the inventions, and the gear box 324 could be incorporated in yet another embodiment. Please observe that the switch simply could mean any electronic circuit or component.

The embodiments described in connection with FIGS. 29, 31 and 32 identify a method and a system for controlling transmission of wireless energy to implanted energy consuming components of an electrically operable apparatus. Such a method and system will be defined in general terms in the following.

A method is thus provided for controlling transmission of wireless energy supplied to implanted energy consuming components of an apparatus as described above. The wireless energy E is transmitted from an external energy source located outside the patient and is received by an internal energy receiver located inside the patient, the internal energy receiver being connected to the implanted energy consuming components of the apparatus for directly or indirectly supplying received energy thereto. An energy balance is determined between the energy received by the internal energy receiver and the energy used for the apparatus. The transmission of wireless energy E from the external energy source is then controlled based on the determined energy balance.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising an apparatus as described above is thus also provided for controlling transmission of wireless energy supplied to implanted energy consuming components of the apparatus. In its broadest sense, the system comprises a control device for controlling the transmission of wireless energy from an energy-transmission device, and an implantable internal energy receiver for receiving the transmitted wireless energy, the internal energy receiver being connected to implantable energy consuming components of the apparatus for directly or indirectly supplying received energy thereto. The system further comprises a determination device adapted to determine an energy balance between the energy received by the internal energy receiver and the energy used for the implantable energy consuming components of the apparatus, wherein the control device controls the transmission of wireless energy from the external energy-transmission device, based on the energy balance determined by the determination device.

Further, the system may comprise any of the following:
A primary coil in the external energy source adapted to transmit the wireless energy inductively to a secondary coil in the internal energy receiver.
The determination device is adapted to detect a change in the energy balance, and the control device controls the transmission of wireless energy based on the detected energy balance change
The determination device is adapted to detect a difference between energy received by the internal energy receiver and energy used for the implantable energy consuming components of the apparatus, and the control device controls the transmission of wireless energy based on the detected energy difference.
The control device controls the external energy-transmission device to decrease the amount of transmitted wireless energy if the detected energy balance change implies that the energy balance is increasing, or vice versa, wherein the decrease/increase of energy transmission corresponds to a detected change rate.
The control device controls the external energy-transmission device to decrease the amount of transmitted wireless energy if the detected energy difference implies that the received energy is greater than the used energy, or vice versa, wherein the decrease/increase of energy transmission corresponds to the magnitude of said detected energy difference.
The energy used for the apparatus is consumed to operate the apparatus, and/or stored in at least one energy storage device of the apparatus.
Where electrical and/or physical parameters of the apparatus and/or physical parameters of the patient are determined, the energy-transmission device transmits the energy for consumption and storage according to a transmission rate per time unit which is determined by the determination device based on said parameters. The determination device also determines the total amount of transmitted energy based on said parameters.
When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.
When the derivative is determined over time of a measured electrical parameter related to the amount of consumed and/or stored energy, the determination device determines the derivative for a monitored voltage and/or current related to the energy balance.
The energy-transmission device comprises a coil placed externally to the human body, and an electric circuit is provided to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. As a result, the energy receiver receiving the transmitted wireless energy has a varied power.
The electric circuit is adapted to deliver the electrical pulses to remain unchanged except varying the first and/or second time intervals.
The electric circuit has a time constant and is adapted to vary the first and second time intervals only in the range of the first time constant, so that when the lengths of the first and/or second time intervals are varied, the transmitted power over the coil is varied.
The electric circuit is adapted to deliver the electrical pulses to be varied by only varying the lengths of first time intervals between successive leading and trailing edges of the electrical pulses.
The electric circuit is adapted to supplying a train of two or more electrical pulses in a row, said train having a first electrical pulse at the start of the pulse train and having a second electrical pulse at the end of the pulse train, and
the lengths of the second time intervals between successive trailing edge of the second electrical pulse in a first pulse train and leading edge of the first electrical pulse of a second pulse train are varied by the first electronic circuit.

The electric circuit is adapted to provide the electrical pulses as pulses having a substantially constant height and/or amplitude and/or intensity and/or voltage and/or current and/or frequency.

The electric circuit has a time constant, and is adapted to vary the first and second time intervals only in the range of the first time constant, so that when the lengths of the first and/or second time intervals are varied, the transmitted power over the first coil are varied.

The electric circuit is adapted to provide the electrical pulses varying the lengths of the first and/or the second, time intervals only within a range that includes the first time constant or that is located relatively close to the first time constant, compared to the magnitude of the first time constant.

According to an embodiment, said wireless energy comprises a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal.

According to an embodiment, said wireless energy comprises one of the following: an electric field, a magnetic field, a combined electric and magnetic field.

According to an embodiment, said control signal comprises one of the following: an electric field, a magnetic field, a combined electric and magnetic field.

According to a further embodiment, said the signal comprises an analogue signal, a digital signal, or a combination of an analogue and digital signal.

According to yet another embodiment, said system further comprises an implantable internal energy source for powering implantable energy consuming components of the apparatus.

According to yet another embodiment, said system further comprises an external energy source for transferring energy in a wireless mode, wherein the internal energy source is chargeable by the energy transferred in the wireless mode.

According to yet another embodiment, said system further comprises a sensor or measuring device sensing or measuring a functional parameter correlated to the transfer of energy for charging the internal energy source, and a feedback device for sending feedback information from inside the patient's body to the outside thereof, the feedback information being related to the functional parameter sensed by the sensor or measured by the measuring device.

According to yet another embodiment, said system further comprises a feedback device for sending feedback information from inside the patient's body to the outside thereof, the feedback information being related to at least one of a physical parameter of the patient and a functional parameter related to the apparatus.

According to yet another embodiment, said system further comprises a sensor and/or a measuring device and an implantable internal control unit for controlling the apparatus in response to information being related to at least one of a physical parameter of the patient sensed by the sensor or measured by the measuring device and a functional parameter related to the apparatus sensed by the sensor or measured by the measuring device.

According to another embodiment, said physical parameter is a pressure or a motility movement.

According to yet another embodiment, said system further comprises an external data communicator and an implantable internal data communicator communicating with the external data communicator, wherein the internal communicator feeds data related to the apparatus or the patient to the external data communicator and/or the external data communicator feeds data to the internal data communicator.

According to yet another embodiment, said system further comprises a motor or a pump for operating the apparatus.

According to yet another embodiment, said system further comprises a hydraulic operation device for operating the apparatus.

According to yet another embodiment, said system further comprises an operation device for operating the apparatus, wherein the operation device comprises a servo designed to decrease the force needed for the operation device to operate the apparatus instead the operation device acting a longer way, increasing the time for a determined action.

According to yet another embodiment, said system further comprises an operation device for operating the apparatus, wherein the wireless energy is used in its wireless state to directly power the operation device to create kinetic energy for the operation of the apparatus, as the wireless energy is being transmitted by the energy-transmission device.

According to yet another embodiment, said system further comprises an energy-transforming device for transforming the wireless energy transmitted by the energy-transmission device from a first form into a second form of energy.

According to an embodiment, said energy-transforming device directly powers implantable energy consuming components of the apparatus with the second form energy, as the energy-transforming device transforms the first form energy transmitted by the energy-transmission device into the second form energy.

According to an embodiment, said second form energy comprises at least one of a direct current, pulsating direct current and an alternating current.

According to yet another embodiment, said system further comprises an implantable accumulator, wherein the second form energy is used at least partly to charge the accumulator.

According to an embodiment, said energy of the first or second form comprises at least one of magnetic energy, kinetic energy, sound energy, chemical energy, radiant energy, electromagnetic energy, photo energy, nuclear energy thermal energy, non-magnetic energy, non-kinetic energy, non-chemical energy, non-sonic energy, non-nuclear energy and non-thermal energy.

According to yet another embodiment, said system further comprises implantable electrical components including at least one voltage level guard and/or at least one constant current guard.

According to yet another embodiment, said system further comprises a control device for controlling the transmission of wireless energy from the energy-transmission device, and an implantable internal energy receiver for receiving the transmitted wireless energy, the internal energy receiver being connected to implantable energy consuming components of the apparatus for directly or indirectly supplying received energy thereto, the system further comprising a determination device adapted to determine an energy balance between the energy received by the internal energy receiver and the energy used for the implantable energy consuming components of the apparatus, wherein the control device controls the transmission of wireless energy from the external energy-transmission device, based on the energy balance determined by the determination device.

According to an embodiment, said determination device is adapted to detect a change in the energy balance, and the control device controls the transmission of wireless energy based on the detected energy balance change.

According to a further embodiment, the determination device is adapted to detect a difference between energy received by the internal energy receiver and energy used for the implantable energy consuming components of the apparatus, and the control device controls the transmission of wireless energy based on the detected energy difference.

According to a further embodiment, the energy-transmission device comprises a coil placed externally to the human body, further comprising an implantable energy receiver to be placed internally in the human body and an electric circuit connected to power the external coil with electrical pulses to transmit the wireless energy, the electrical pulses having leading and trailing edges, the electric circuit adapted to vary first time intervals between successive leading and trailing edges and/or second time intervals between successive trailing and leading edges of the electrical pulses to vary the power of the transmitted wireless energy, the energy receiver receiving the transmitted wireless energy having a varied power.

According to a further embodiment, the electric circuit is adapted to deliver the electrical pulses to remain unchanged except varying the first and/or second time intervals.

According to a further embodiment, the electric circuit has a time constant and is adapted to vary the first and second time intervals only in the range of the first time constant, so that when the lengths of the first and/or second time intervals are varied the transmitted power over the coil is varied.

According to a further embodiment, the system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil, wherein the external second coil of the energy transmitter transmits wireless energy which is received by the first coil of the energy receiver, the system further comprising a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off.

According to a further embodiment, the system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil, wherein the external second coil of the energy transmitter transmits wireless energy which is received by the first coil of the energy receiver, the system further comprising a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factors between the first and second coils.

According to an embodiment, the transmitted energy may be regulated depending on the obtained coupling factor.

According to a further embodiment, said external second coil is adapted to be moved in relation to the internal first coil to establish the optimal placement of the second coil, in which the coupling factor is maximized.

According to a further embodiment, said external second coil is adapted to calibrate the amount of transferred energy to achieve the feedback information in the determination device, before the coupling factor is maximized.

According to yet another embodiment, the mechanical device comprises a mechanical multi step locking mechanism, locking the mechanical device in its new position after adjustment. An example is illustrated in FIG. 10 where FIG. 10*a* shows schematically a detail view of a device (700) according to the invention, said device comprising at least one hydraulic piston (701) and two actuators (702, 703). In this embodiment one actuator is attached to the housing of the device, whereas the other is moving. In order to prevent an actuator from returning to a previous position, for example when temporarily subjected to an increased stress, the housing has an aperture (705) and the actuator has cone-shaped flanges (704) allowing an outward movement of the actuator, but substantially preventing an inward movement.

FIG. 10*b* shows an alternative embodiment where, in a device (800) according to the invention, two pistons (801, 802) are provided in a housing. The pistons are connected to two actuators (805, 806), which in turn are engaged to anchoring devices (not shown), On the inside, said housing has a pattern of protrusions, vests or barbs, allowing said pistons to move in one direction, preferably outward, but substantially preventing an inward movement.

According to yet another embodiment, the mechanical multi step locking mechanism comprises at least one of a sprint, a elongated structure using the principle of saw teeth, flanges, barbs or a bonnet band, a nut, a gearbox, or a spring loaded locking principle.

According to a further embodiment of the system, the device comprises a control device.

According to another embodiment, said control device follows a program of incremental changes, set before the device is implanted.

According to another embodiment, said control device follows a program of incremental changes, communicated to the control device after implantation and/or during the treatment.

According to another embodiment, said control device comprises an external control unit and an implantable receiver suitable for wireless communication with said external control unit, having a transmitter located outside the body.

According to another embodiment, said control device controls incremental changes of the adjustment device, communicated to the receiver after implantation and/or during the treatment by using said external control unit.

According to a preferred embodiment, said device is flexible to allow introduction into the medullar cavity. Alternatively or in combination therewith, said device is at least partly elastic. Alternatively or in combination therewith, said device comprises a spring. Alternatively or in combination therewith, said device is adapted to regain its shape after having been bent.

According to another embodiment, freely combinable with the other embodiments presented herein, the anchoring device comprises a thread for engaging and stabilizing the anchoring device in relation to the bone.

According to a further embodiment, the anchoring device comprises an expandable part expanding at least partially perpendicular to the longitudinal extension of the elongated device for engaging and stabilizing the anchoring device in relation to the bone. This embodiment is illustrated in FIG. 33, which schematically shows a device 900, having two end-portions or anchoring means 902 and 903, for example elastic and expandable means, here shown as activated externally, by a key or knob 901, having a portion insertable into the device 900 and engaging a mechanism activating and in particular expanding the anchoring means 902 and 903.

The views I, II and III show in turn how the anchoring means 902 and 903 are in their initial, non-expanded state, allowing insertion into a cavity; how they can be activated and expanded; and how they when expanded engage the surrounding cavity and allow the operation of the device for bone adjustment.

According to an alternative embodiment, schematically shown in FIG. 34, a device 920 comprises anchoring means in the form of an arrangement of flanges 922 and 923. An external device, here shown as a wire 921 having an end portion capable of engaging a mechanism for activation of 922 and 923, is brought in operational contact with the device, and the anchoring devices activated. When activate, the anchoring devices engage the surrounding cavity and allow the operation of the device for bone adjustment.

Figure 38:
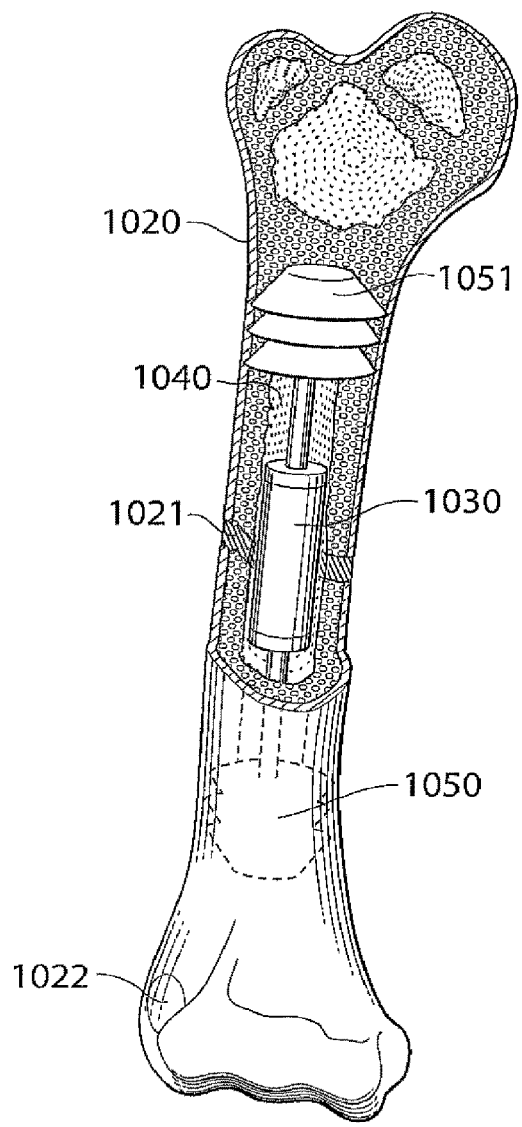

FIG. 38 shows a partial cut-out view of a bone 1020 having a fracture zone 1021, with an implantable device according to an embodiment of the invention implanted in the medullar cavity 1040, said device comprising a body 1030 and two anchoring devices 1050 and 1051. The entry hole 1022 is shown as sealed or closed, for example with bone cement, and the adjustment device is shown in extended and operational condition, where the anchoring devices 1050 and 1051 securely engage the bone.

According to a further embodiment, the adjustment device is adapted to comprise torsion of a bone. Alternatively, or in combination, said adjustment device is adapted to change the angle of a bone.

According to a further embodiment, said adjustment device comprises at least two parts, wherein the parts are adapted to rotate in relation to each other. Preferably said relative rotation is anchored by said at least two anchoring devices.

According to another embodiment, freely combinable with the other embodiments presented herein, said adjustment device is adapted to change the angle of a bone.

According to further embodiment, freely combinable with the other embodiments presented herein, said adjustment device comprises at least two parts, wherein the parts are adapted to be positioned at an angle in relation to each other.

This is illustrated schematically in FIG. 40 which shows an embodiment where the implanted adjustment device comprises at least two parts 2100 and 2200, wherein the parts are adapted to be positioned at an angle in relation to each other, and/or rotated in relation to each other. The movement is achieved by the provision of a joint, here shown as a semicircular or hemispherical element 2250, attached to an operation device 2260, adapted to turn or rotate the element 2250 in relation to the part 2200. The element 2250 is also operationally engaged to the part 2100, where an adjustment device 2150 is adapted to engage said element, in order to change the angle between the parts 2100 and 2200. Preferably said operation device 2260 and said adjustment device 2260 each comprise a motor, and optionally also a gear box and a control unit, as described in the context of other embodiments herein.

The arrows schematically indicate the possible directions of movement of the parts shown in FIG. 40, but it is understood that the parts can be angled, tilted or rotated in relation to each other as desired.

According to a further embodiment, said two or more anchoring devices are adapted to engage and carry weight purely on the inside of the bone.

According to yet another embodiment, said two or more anchoring devices are adapted to engage with and carry weight to the bone without penetrating to the outside of the bone.

According to yet another embodiment, said two or more anchoring devices are adapted to engage and carry weight purely on the outside of the bone.

According to another embodiment, freely combinable with any embodiment presented herein, said device comprises a sensor directly or indirectly sensing the position of the adjustment device.

According to a further embodiment, the device comprises a feedback transmitter adapted to transmit information received directly or indirectly from said sensor out from the human body, said transmitted information adapted to be received by a external control unit and relating to the position of the adjustment device.

According to another embodiment of the device, said operation device is a motor operated as a three-phase motor. Alternatively, said operation device is a motor operated as a two- or more phase motor.

According to another embodiment, freely combinable with any embodiment presented herein, said device comprises a gearbox connected to the motor, a motor package, wherein the outgoing speed from the motor package is lower than the speed by said motor alone, accomplished by said gearbox.

According to another embodiment, freely combinable with any embodiment presented herein, said device comprises an electrical speed controller connected to the motor, a motor package, wherein the outgoing speed of the motor in said motor package is decreased by said electrical speed controller.

According to any of the above embodiments, the motor is a rotational motor and the outgoing speed of the motor package is decreased to less than 100 turns per second, alternatively decreased to less than 10 turns per second, alternatively to less than 1 turn per second, or alternatively to less than 0.1 turn per second, or alternatively to less than 0.01 turn per second, or alternatively to less than 0.001 turn per second.

According to another embodiment, freely combinable with any embodiment presented herein, said device comprises an electrical speed controller connected to the motor, a motor package, wherein the outgoing speed of the motor of said motor package is controlled by said electrical speed controller.

According to any of the above embodiments, the motor is a linear motor and the outgoing speed of the motor package is less than 1 mm per second, alternatively less than 0.1 mm per second, or alternatively less than 0.01 mm per second, or alternatively less than 0.001 mm per second, or alternatively less than 0.0001 mm per second, or less than 0.00001 mm per second.

The construction of a device according to the invention is illustrated also in FIG. 35, schematically showing an embodiment of the device 930, comprising two telescopically arranged parts 932 and 933, housing a longitudinal threaded central shaft or axis 937 and a motor or gear arrangement 938 acting thereon, transforming rotational force into longitudinal force and extension or contraction of the device.

Further, FIG. 36 shows another related embodiment where the device comprises three main parts, a central section 935, and two telescopically arranged end sections 934 and 936, each connected to a longitudinal threaded central shaft or axis 939 end 940 through a motor or gear arrangement 941 and 942.

Finally, FIG. 37A and B show embodiments where a device for bone adjustment according to the present invention, schematically shown as 1000 and 1010, is enclosed in an elastic outer cover 1001, or an expandable outer cover 1011, the expansion made possible by folds 1012, the covers protecting the device from direct contact with tissues and body fluids.

Said elastic, flexible or expandable cover is preferably made of a polymeric material generally recognised as safe and approved for surgical use, and can be suitably coated to minimize tissue irritation. Non-limiting examples of the material include silicon, polyurethane and TEFLON®, and non-limiting examples of suitable coatings include atomized metal coatings, and polymeric coatings, such as PARYLENE®.

It should be noted that the above embodiments, and features appearing in the individual embodiments, are freely combinable.

EXAMPLES

There are animal models for the investigation of fracture healing, such as a rabbit fibula model, a sheep model for fracture treatment in osteoporosis, a murine femur fracture model. It is conceived that the inventive device and method can be tested in existing animal models, preferably models involving the use of larger mammals, such as sheep, pig, dog, monkey etc.

There are also non-invasive methods for the evaluation of bone fracture healing, see e.g. a review article (Protopappas et al., 2008) describing quantitative ultrasonic monitoring of bone fracture healing.

In a suitable animal model, a test animal is anaesthetised, and a bone dissected and fractured. When dissecting a bone, care is taken to cause minimal tissue damage, e.g. by folding or pulling tissue to the side instead of removing it from its location. Pins or other anchoring devices are fixed in the bone on both sides of the fracture, and a device according to the invention attached to said anchoring devices. The tissue is replaced carefully, preferably layer by layer, and the body of the animal closed. After a suitable initial healing period, the fracture zone is adjusted non-invasively. Parameters such as bone healing, pain and signs of infection or inflammation are observed regularly. Following euthanasia, the bone is dissected and the fracture zone analysed.

The experiment can be repeated, with necessary modifications, in the same or in a different animal model, for evaluating the adjustment of the curvature of the spine, realigning a joint, changing the curvature of a bone, or the like.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

REFERENCES

Consolo U, Bertoldi C, Zaffe D, Intermittent loading improves results in mandibular alveolar distraction osteogenesis, *Clin Oral Implants Res*. 2006 April; 17(2):179-87.

Gabbay J S. Zuk P A, Tahernia A, Askari M, O'Hara C M, Karthikeyan T, Azari K, Hollinger J O, Bradley J P, In vitro microdistraction of preosteoblasts: distraction promotes proliferation and oscillation promotes differentiation, *Tissue Eng*. 2006 November; 12(11):3055-65.

Hente R, Füchtmeier B, Schlegel U, Ernstherger A, Perren S M., The influence of cyclic compression and distraction on the healing of experimental tibial fractures. *J Orthop Res.*, 2004 July; 22(4):709-15

Protopappas V C, Vavva M G, Fotiadis D I, Malizos K N, IEEE Trans Ultrason Ferroelectr Freq Control. 2008; 55(6): 1243-55

Snela S, Kisiel J, Gregosiewicz A, Dziubiński F., Biomechanical studies of forces occurring in the Ilizarov and Orthofix apparatuses during limb lengthening by distractive osteogenesis, *Chir Narzadow Ruchu Ortop Pol* 2000; 65(2): 155-66. [Article in Polish]

The invention claimed is:

1. A device for bone adjustment in a mammal, the device comprising:
   a bone adjusting housing, sized and adapted to be implanted entirely intramedullary in a femoral or tibial bone in said mammal said housing comprising
   two or more anchoring devices adapted to be attached to the femoral or tibial bone in said mammal,
   an adjustment device for exerting a force on said two or more anchoring devices, said adjustment device being adapted to postoperatively adjust at least one of a distance between or orientation of, at least two of said two or more anchoring devices,
   an operation device comprising a motor, wherein said operation device is adapted to operate said adjustment device,
   a gearbox connected to the motor, wherein an outgoing speed from the gear box is lower than a speed by the motor alone, accomplished by the gearbox, and wherein the outgoing speed of the gearbox is less than 10 turn per second during normal operation, and wherein said device for bone adjustments further comprises
   a control device adapted to control the operation device, wherein the control device is programmed to control the device according to a pre-programmed time-schedule comprising a program of incremental changes.

2. The device according to claim 1, wherein said bone adjustment is a lengthening of the bone, a healing of a fracture, a changing of a bone angle, a reshaping of the bone, a compression of the bone, a torsion of the bone or a combination thereof.

3. The device according to claim 1, wherein said two or more anchoring devices are adapted to at least one of:
   engaging and stabilizing the adjustment device using a thread in relation to the bone,
   engage and carry weight only on the outside of the bone,
   engage and carry weight only on the inside of the bone, and
   anchoring a relative rotation of the adjustment device including at least two parts adapted to rotate in relation to each other.

4. The device according to claim 3, wherein said at least two or more anchoring devices are chosen from a screw, an adhesive, a barb construction, a saw-tooth construction, an expandable element, combinations thereof or other mechanical connecting members.

5. The device according to claim 1, wherein the force exerted by the adjustment device is configured to be at least one of:

a longitudinal force, extending a length of the bone, directed to end portions of a medullar cavity, a longitudinal force, adjusting an angle or curvature of the bone, and applied torque to the bone, adjusting a torsion of the bone along a longitudinal axis of the bone.

6. The device according to claim 1, wherein said device is flexible.

7. The device according to claim 2, wherein the adjustment device comprises a hydraulic device for said bone adjustment, to control the amount of force exerted by the device onto said two or more anchoring devices, wherein the hydraulic device comprises at least one of:

a cylinder and piston.

a mechanical multi step locking mechanism, locking the hydraulic device in a new position after adjustment, a mechanical multi step locking mechanism, locking the hydraulic device in a new position after adjustment, wherein the mechanical multi step locking mechanism comprises at least one of a sprint, an elongated structure using the principle of saw teeth, flanges, barbs or a bonnet band, a nut, a gearbox, or a spring loaded locking principle, hydraulic fluid and a reservoir containing said hydraulic fluid, adapted to move said hydraulic fluid to said adjustment device, hydraulic fluid and a reservoir containing said hydraulic fluid, adapted to move said hydraulic fluid to said adjustment device, wherein the hydraulic fluid is moved from said reservoir to said adjustment device by using a pre-pressurized reservoir or a pump, a device positioning system such as a fluid volume or flow measurement or any other sensor input to see a position of the adjustment device.

8. The device according to claim 1, wherein said control device follows a program of incremental changes, set before the device is implanted.

9. The device according to claim 1, wherein said control device follows a program of incremental changes, communicated to the control device after implantation and/or during the treatment.

10. The device according to claim 1, wherein said control device comprises an external control unit and an implantable receiver suitable for wireless communication with said external control unit, having a transmitter located outside a body.

11. The device according to claim 1, wherein said adjustment is adapted to perform: a correction of a limb discrepancy caused by a congenital condition or deformation, a correction of a limb discrepancy caused by previous trauma, a changing of the curvature of the bone, a changing of an angle between the diaphysis and the epiphysis, a changing the thickness of the bone, a changing of a curvature of a spine, an adjoining of vertebrae adapted to change the curvature of the spine, and an adjoining of vertebrae adapted to relieve a herniated lumbar disc or the like.

12. The device according to claim 1, wherein said adjustment device is, at least one of:

adapted to implement torsion of the bone, adapted to change a angle of the bone, adapted to have at least two parts to rotate in relation to each other, wherein said adjustment device comprises said at least two parts, the relative rotation being anchored by at least two of said two or more anchoring devices, adapted to have at least two parts angled in relation to each other, wherein said adjustment device comprises at least two parts, adapted to change a curvature of the bone, adapted to change a curvature of the spine, adapted to adjoining vertebrae, adapted to change at least one of; the curvature of the spine and to relieve a herniated lumbar disc or the like, and adapted to non-adjoining vertebrae, adapted to at least one of: change the curvature of the spine or relieve a herniated lumbar disc or the like.

13. The device according claims 1, wherein the control device is adapted to, at least one of:

control incremental changes of the adjustment device, communicated to a receiver after implantation and/or during a treatment by using an external control unit and an implantable receiver suitable for wireless communication with said external control unit, having a transmitter located outside the mammal, regulate the device non-invasively by manually pressing at least one subcutaneous switch, whereby the operation of the device is switched on and off, further comprising an implantable internal energy source for powering implantable energy consuming components of the device, and regulate the device non-invasively by manually pressing at least one subcutaneous switch, wherein the at least one subcutaneous switch sends information to an internal control unit to perform a certain predetermined performance.

14. The device according to claim 1, wherein the adjustment device comprising, at least one of:

a mechanical device for said bone adjustment comprising at least one nut and screw, a mechanical device for said bone adjustment comprises a servo mechanism or mechanical amplifier, a hydraulic or mechanical device for said bone adjustment, which comprising a mechanical multi step locking mechanism, locking the hydraulic or mechanical device in a new position after adjustment, and a mechanical or hydraulic device for said bone adjustment, which comprising a mechanical multi step locking mechanism, locking the hydraulic or mechanical device in a new position after adjustment, comprising at least one of; a sprint, an elongated structure using the principle of saw teeth, flanges, barbs or a bonnet band, a nut, a gearbox, or a spring loaded locking principle.

15. The device according to claim 1, wherein the motor is at least one of:

operated as a three-phase motor, operated as a two or more phase motor, connected to an electric speed controller wherein the outgoing speed of the motor is decreased by said electrical speed controller, a rotational motor, and a linear motor.

16. The device according to claim 1, wherein said device is, at least one of:

flexible to allow introduction into a medullar cavity, at least partly elastic and flexible to allow introduction into a medullar cavity, comprising a spring and is flexible to allow introduction into a medullar cavity, regaining its shape after having been bent, comprising a locking device, which allows extension of the device but substantially prevents contraction, comprising a sensor directly or indirectly sensing a position of the adjustment device.

17. The device according to claim 1, wherein the device comprising a sensor directly or indirectly sensing a position of the adjustment device, the device comprising a feedback transmitter adapted to transmit information received direct or indirect from said sensor out from the mammal, said transmitted information adapted to be received by an external control unit and relating to the position of the adjustment device.

18. The device according to claims 1, being part of a system, comprising at least one of:
a sensor or measuring device sensing or measuring a functional parameter correlated to the transfer of energy for charging an internal energy source, and a feedback device for sending feedback information from inside the mammal to the outside thereof, the feedback information being related to the functional parameter sensed by the sensor or measured by the measuring device, further comprising an implantable internal energy source for powering implantable energy consuming components of the device, and an external energy source for transferring energy in a wireless mode, wherein the internal energy source is chargeable by the energy transferred in the wireless mode,
a feedback device for sending feedback information from inside the mammal to the outside thereof, the feedback information being related to at least one of a physical parameter of the mammal and a functional parameter related to the device,
a sensor and/or a measuring device and an implantable internal control unit for controlling the device in response to information being related to at least one of a physical parameter of the mammal sensed by the sensor or measured by the measuring device and a functional parameter related to the device sensed by the sensor or measured by the measuring device,
an external data communicator and an implantable internal data communicator communicating with the external data communicator, wherein the internal communicator feeds data related to the device or the mammal to the external data communicator, the external data communicator feeds data to the internal data communicator, or the internal communicator feeds data related to the device or the mammal to the external data communicator and the external data communicator feeds data to the internal data communicator.

19. The device according to claim 1, being part of a system, comprising at least one of:
at least one switch implantable in the mammal for manually and non-invasively controlling the device,
a wireless remote control for non-invasively controlling the device.
a hydraulic device having an implantable hydraulic reservoir, which is hydraulically connected to the device, wherein the device is adapted to be non-invasively regulated by manually pressing the hydraulic reservoir.

20. The device according to claim 1, being part of a system comprising at least one of:
a wireless energy-transmission device for non-invasively energizing implantable energy consuming components of the device with wireless energy,
an implantable internal energy source for powering implantable energy consuming components of the device, and
an external energy source for transferring energy in a wireless mode and an implantable internal energy source for powering implantable energy consuming components of the device, wherein the internal energy source is chargeable by the energy transferred in the wireless mode,
implantable electrical components including at least one voltage level guard and/or at least one constant current guard,
an energy-transforming device for transforming the wireless energy transmitted by the energy-transmission device from a first form into a second form of energy, wherein the second form energy is used at least partly to charge an accumulator,
an operation device for operating the device, wherein the wireless energy is used in a wireless state to directly power the operation device to create kinetic energy for the operation of the device, as the wireless energy is being transmitted by the energy-transmission device, and
an energy-transforming device for transforming the wireless energy transmitted by the energy-transmission device from a first form into a second form of energy, wherein the energy-transforming device directly powers implantable energy consuming components of the device with the second form energy, as the energy-transforming device transforms the first form energy transmitted by the energy-transmission device into the second form energy.

21. The device according to claim 1, wherein the adjustment device comprises a hydraulic device for said bone adjustment, the hydraulic device is adapted to at least one of:
be stabilized when the bone adjustment is completed,
be filled with a material which stabilizes a position of the adjustment device and permanents the distance between said two or more anchoring devices,
be stabilized when the bone adjustment is completed, wherein the material is chosen from a curable foam, a curable gel, a polymer or polymer mixture which solidifies, crosslinks or otherwise attains and retains a stable volume,
be stabilized when the bone adjustment is completed, wherein the hydraulic fluid used in said device is a material chosen from a curable foam, a curable gel, a polymer or polymer mixture which solidifies, crosslinks or otherwise attains and retains a stable volume when the curing, solidification, crosslinking or other reaction is initiated by the user, and
be stabilized when the bone adjustment is completed, wherein the material is chosen from a curable foam, a curable gel, a polymer or polymer mixture which solidifies, crosslinks or otherwise attains and retains a stable volume, is added to the device, partially or completely replacing the hydraulic fluid.

22. The device according to claim 1, wherein said two or more anchoring devices are adapted to engage and carry weight purely on an inside of the bone, wherein at least two of said two or more anchoring devices are adapted to engage with and carrying weight to the bone without penetrating to the outside of the bone, from an intramedullary cavity of the bone.

23. The device according to claim 1, wherein at least one of said two or more anchoring devices comprises an expandable part adapted to expand at least partially perpendicular to the longitudinal extension of the elongated device for engaging and stabilizing the anchoring device in relation to the bone.

24. The device according to claim 1, wherein the motor is a rotational motor and the outgoing speed of the gear box is decreased to less than 1 turn per second.

25. The device according to claim 1, wherein the motor is a rotational motor and the outgoing speed of the gearbox is decreased to less than: 0.1 turn per second, 0.01 turn per second, or 0.001 turn per second.

26. The device according to claim 1, wherein the device is adapted to be exerting an intermittent, oscillating force, or intermittent and oscillating force according to a preset program or according to instructions transmitted wirelessly to the device.

27. The device according to claim 26, wherein the intermittent, oscillating force, or intermittent and oscillating force comprises an implanted hydraulic device.

28. The device according to claim 1, wherein the device is adapted to be implanted intramedullary in a body of said mammal, wherein said device is a hydraulic device exerting a force to at least two of said at least two anchoring devices adapted to be anchored in said bone, and wherein the control device is configured to control the amount of force exerted by the device.

29. The device according to claim 1, wherein the adjustment device comprises an extension device, adapted to be capable of longitudinal movement and in particular capable of exerting a force longitudinally between two or more points, wherein the extension device can be a hydraulic device, an electronic device, a mechanical device, or a combination of two or more thereof.

30. The device according to claim 1, further comprising a hydraulic device, adapted to bring longitudinal force on elements in the device, such as hydraulic cylinders and the like, transmitted by a hydraulic fluid bringing the longitudinal force.

31. The device according to claim 1, wherein the hydraulic device comprises a device positioning system to see a position of the adjustment device.

32. The device according to claim 1, wherein the adjustment device adapted to exert force on said two or more anchoring devices to adjust the distance between or orientation of at least two of said two or more anchoring devices, wherein said two or more anchoring devices and said adjustment device are implanted intramedullary in said mammal and wherein said adjustment device is constructed to postoperatively adjust said distance.

33. The device according to claim 1, comprising an electrical speed controller connected to the motor, a motor package, wherein the outgoing speed of the motor in said motor package is controlled by said electrical speed controller,
wherein the motor is a linear motor and the outgoing speed of the gear box is less than at least one of:
less than 1 mm per second,
less than 0.1 mm per second,
less than 0.01 mm per second,
less than 0.001 mm per second,
less than 0.0001 mm per second, and
less than 0.00001 mm per second.

34. The device according to claim 1, being part of a system, comprising a wireless energy-transmission device for non-invasively energizing implantable energy consuming components of the device with wireless energy, further comprising a control device for controlling the transmission of wireless energy from the energy-transmission device, and an implantable internal energy receiver for receiving the transmitted wireless energy, the internal energy receiver being connected to implantable energy consuming components of the apparatus for directly or indirectly supplying received energy thereto, the system further comprising a determination device adapted to determine an energy balance between the energy received by the internal energy receiver and the energy used for the implantable energy consuming components of the device, wherein the control device controls the transmission of wireless energy from the external energy-transmission device, based on the energy balance determined by the determination device.

35. The device according to claim 1, being part of a system, comprising an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil, wherein the external second coil of the energy transmitter transmits wireless energy which is received by the first coil of the energy receiver, the system further comprising a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factors between the first and second coils.

36. A method for adjustment of a bone adjusting device in a mammal, the device comprising:
a bone adjusting housing, sized and adapted to entirely be implanted intramedullary in a femoral or tibial bone in said mammal, said housing comprising
two or more anchoring devices adapted to be attached to the femoral or tibial bone in said mammal,
an adjustment device for exerting a force on said two or more anchoring devices, said adjustment device being adapted to postoperatively adjust at least one of a distance between or orientation of, at least two of said two or more anchoring devices,
an operation device comprising a motor, wherein said operation device is adapted to operate said adjustment device,
a gearbox connected to the motor, wherein an outgoing speed from the gear box is lower than a speed by the motor alone, accomplished by the gearbox, and wherein said method for controlling the device for bone adjustments comprises
controlling the operation device according to a pre-programmed time-schedule with a outgoing speed of the gearbox that is less than 10 turn per second during.

* * * * *